US010626453B2

United States Patent
Huber

(10) Patent No.: US 10,626,453 B2
(45) Date of Patent: Apr. 21, 2020

(54) PORTABLE NUCLEIC ACID ANALYSIS SYSTEM AND HIGH-PERFORMANCE MICROFLUIDIC ELECTROACTIVE POLYMER ACTUATORS

(71) Applicant: SRI International, Menlo Park, CA (US)

(72) Inventor: David E. Huber, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 456 days.

(21) Appl. No.: 15/304,030

(22) PCT Filed: Apr. 14, 2015

(86) PCT No.: PCT/US2015/025836
§ 371 (c)(1),
(2) Date: Oct. 13, 2016

(87) PCT Pub. No.: WO2015/160864
PCT Pub. Date: Oct. 22, 2015

(65) Prior Publication Data
US 2017/0030859 A1     Feb. 2, 2017

Related U.S. Application Data

(60) Provisional application No. 61/979,377, filed on Apr. 14, 2014, provisional application No. 62/041,430, (Continued)

(51) Int. Cl.
*G01N 27/447*     (2006.01)
*B01L 3/00*     (2006.01)
(Continued)

(52) U.S. Cl.
CPC ........ *C12Q 1/686* (2013.01); *B01L 3/502715* (2013.01); *B01L 3/502723* (2013.01);
(Continued)

(58) Field of Classification Search
CPC ..... C12Q 1/686; B01L 7/52; B01L 3/502746; B01L 3/502723; B01L 3/502715;
(Continued)

(56) References Cited

U.S. PATENT DOCUMENTS 5,981,956 A    11/1999   Stern
2004/0234401 A1    11/2004   Banister
(Continued)

OTHER PUBLICATIONS

EPO. Supplementary Partial European Search Report dated Feb. 13, 2018, for related European Patent Application No. 15780486.5, 3 pages.
(Continued)

*Primary Examiner* — Gurpreet Kaur
(74) *Attorney, Agent, or Firm* — Dicke, Billig & Czaja, PLLC

(57) ABSTRACT

Devices, systems and methods for the parallel detection of a set of distinct nucleic acid sequences use multiple sequence amplification and simultaneous hybridization readout. An automated nucleic acid analysis system comprises in microfluidic connection sample lysis, purification, PCR and detection modules configured to detect in parallel distinct nucleic acid sequences via multiple sequence amplification and simultaneous microarray hybridization readout. High performance microfluidic electroactive polymer (µEAP) actuators comprising a dead-end fluid chamber in which a surface of the chamber is an electrode covered with an EAP layer of dielectric elastomer are configured for particle sorting.

21 Claims, 13 Drawing Sheets

Related U.S. Application Data filed on Aug. 25, 2014, provisional application No. 62/081,525, filed on Nov. 18, 2014.

(51) Int. Cl.
| | |
|---|---|
| *B01L 7/00* | (2006.01) |
| *C12Q 1/686* | (2018.01) |
| *C40B 60/12* | (2006.01) |

(52) U.S. Cl.
CPC ... *B01L 3/502738* (2013.01); *B01L 3/502746* (2013.01); *B01L 7/52* (2013.01); *G01N 27/4473* (2013.01); *G01N 27/44791* (2013.01); *B01L 2200/028* (2013.01); *B01L 2200/0684* (2013.01); *B01L 2200/10* (2013.01); *B01L 2300/0654* (2013.01); *B01L 2300/087* (2013.01); *B01L 2300/0816* (2013.01); *B01L 2300/0819* (2013.01); *B01L 2300/0887* (2013.01); *B01L 2300/168* (2013.01); *B01L 2300/1822* (2013.01); *B01L 2400/0487* (2013.01); *B01L 2400/082* (2013.01); *C40B 60/12* (2013.01)

(58) Field of Classification Search
CPC ......... B01L 2200/10; B01L 2200/0684; B01L 2200/0652; B01L 2200/0668; B01L 2300/0654; B01L 2300/0816; B01L 2300/1822; B01L 2300/168; B01L 2300/0887; B01L 2300/087; B01L 2300/0819; B01L 2400/0487; B01L 2400/082; B01L 2400/0415; B01L 2400/0421; B01L 2400/0424; G01N 27/4473; G01N 27/221; G01N 27/447; G01N 27/44791; C40B 60/12; B03C 5/00; B03C 5/022; B03C 5/024; B03C 5/026

See application file for complete search history.

(56) References Cited

U.S. PATENT DOCUMENTS

| | | |
|---|---|---|
| 2007/0057211 A1 | 3/2007 | Bahlman et al. |
| 2009/0066315 A1 | 3/2009 | Hu et al. |
| 2010/0176322 A1 | 7/2010 | Heim et al. |
| 2011/0312615 A1 | 12/2011 | Azimi et al. |
| 2012/0273702 A1 | 11/2012 | Culbertson et al. |
| 2013/0155403 A1 | 6/2013 | Tan et al. |

OTHER PUBLICATIONS

Chun H. Chen et al. "Microfluidic cell sorter with integrated piezoelectric actuator." Biomed Microdevices, 11:1223-1231 (Aug. 1, 2009).

David E. Huber et al. "Microfluidic Electroactive Polymer-Actuated Cell Sorting." 18th Int'l Conference on Miniaturized Systems for Chemistry and Life Sciences, pp. 434-436 (Oct. 26-30, 2014), San Antonio, Texas, USA.

H. M. Shapiro, Practical Flow Cytometry, John Wiley & Sons, 2003.

Piyasena, Menake E., and Steven W. Graves. "The intersection of flow cytometry with microfluidics and microfabrication." Lab on a Chip 14.6 (2014): 1044-1059.

Chen, Yue, et al. "3D pulsed laser-triggered high-speed microfluidic fluorescence-activated cell sorter." Analyst 138.24 (2013): 7308-7315.

Price, Alexander K., Kristen M. Anderson, and Christopher T. Culbertson. "Demonstration of an integrated electroactive polymer actuator on a microfluidic electrophoresis device." Lab on a Chip 9.14 (2009): 2076-2084. Abstract only.

Murray, Coleman, et al. "Electra-adaptive microfluidics for active tuning of channel geometry using polymer actuators." Microfluidics and nanofluidics 14.1-2 (2013): 345-358.

Di Carlo, Dino, et al. "Continuous inertial focusing, ordering, and separation of particles in microchannels." Proceedings of the National Academy of Sciences 104.48 (2007): 18892-18897.

Niemz, Angelika, Tanya M. Ferguson, and David S. Boyle. "Point-of-care nucleic acid testing for infectious diseases." Trends in biotechnology 29.5 (2011): 240-250.

Bissonnette, Luc, and Michel G. Bergeron. "Infectious disease management through point-of-care personalized medicine molecular diagnostic technologies." Journal of personalized medicine 2.2 (2012): 50-70.

Foudeh, Amir M., et al. "Microfluidic designs and techniques using lab-on-a-chip devices for pathogen detection for point-of-care diagnostics." Lab on a Chip 12.18 (2012): 3249-3266.

Easley, Christopher J., et al. "A fully integrated microfluidic genetic analysis system with sample-in-answer-out capability." Proceedings of the National Academy of Sciences 103.51 (2006): 19272-19277.

Xu, Guolin, et al. "A self-contained all-in-one cartridge for sample preparation and real-time PCR in rapid influenza diagnosis." Lab on a Chip 10.22 (2010): 3103-3111. Abstract only.

Ferguson, B. Scott, et al. "Genetic analysis of H1N1 influenza virus from throat swab samples in a microfluidic system for point-of-care diagnostics." Journal of the American Chemical Society 133.23 (2011): 9129-9135.

Lam, Brian, et al. "Polymerase chain reaction-free, sample-to-answer bacterial detection in 30 minutes with integrated cell lysis." Analytical chemistry 84.1 (2011): 21-25.

Chen, Dafeng, et al. "An integrated, self-contained microfluidic cassette for isolation, amplification, and detection of nucleic acids." Biomedical microdevices 12.4 (2010): 705-719.

Chen, Zongyuan, et al. "Development of a generic microfluidic device for simultaneous detection of antibodies and nucleic acids in oral fluids." BioMed research international 2013 (2013).

Schumacher, Soeren, et al. "Highly-integrated lab-on-chip system for point-of-care multiparameter analysis." Lab on a Chip 12.3 (2012): 464-473. Abstract only.

Akbari, Samin. Arrays of dielectric elastomer microactuators for cell mechanotransduction. Diss. École Polytechnique Fédérale De Lausanne, 2013.

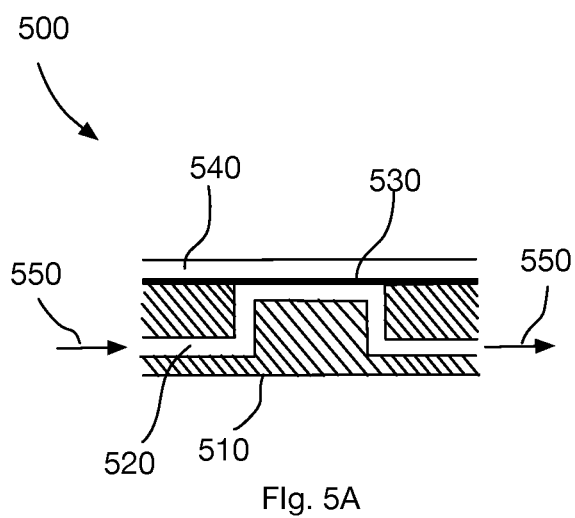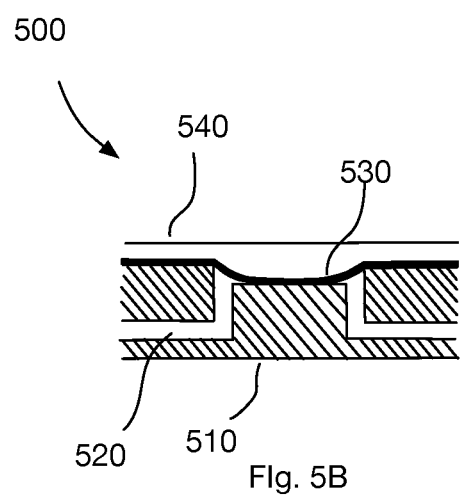

PORTABLE NUCLEIC ACID ANALYSIS SYSTEM AND HIGH-PERFORMANCE MICROFLUIDIC ELECTROACTIVE POLYMER ACTUATORS

This application claims priority to Ser. No. 62/081,525; filed Nov. 18, 2014, to 62/041,430; filed Aug. 25, 2014, and to Ser. No. 61/979,377; filed Apr. 14, 2014.

This invention was made with government support under Defense Advanced Research Projects Agency under contract no. HR0011-14-C-0082. The government has certain rights in the invention.

INTRODUCTION

The integration of sample preparation with amplification and detection in an easy-to-use system remains a significant challenge for nucleic acid diagnostics. [1] A number of systems have been approved by the FDA as "moderate complexity" devices for use in near-POC applications [2], including Cepheid's GeneXpert platform, Nanosphere's Verigene platform, the BD Max System from Becton, Dickinson and Company, and Liat's "lab-in-a-tube" disposable device.

The research literature is rife with examples of pathogen detection techniques and devices; however, no one has been able to develop a multiplex, automated, integrated "sample to result" system, configured to accept raw biological samples. [3] An early example used electrophoretic separation and laser-induced fluorescence to detect the presence of pathogenic DNA extracted and amplified from whole blood [4]. Xu et al. [5] used real-time fluorescence readout during amplification to detect as few as 100 copies/µl. Ferguson et al. [6] electrochemically detected viral RNA hybridized to PNA probes on nanostructured electrodes in the presence of an electrocatalytic buffer, while Lam et al. [7] detected hybridization of amplified ssDNA to redox labeled molecular probes deposited on a gold electrode. Ferguson [6] demonstrated an LOD equivalent to 10 TCID50 (tissue culture infective dose), which was 4 orders of magnitude less than clinical titer values. Lam [7] demonstrated an LOD of 1 bacteria/µl, although a concentration of 100 CFU/µl was used when performing analysis on a spiked urine sample. Two groups used a lateral-flow sandwich assay as the basis for their nucleic acid detection [8, 9], and a Fraunhofer Institutes ivD-Platform [10] used a modular platform.

For decades the Department of Defense (DoD) has recognized the need for field-portable biological analysis. Initially, the need was for identifying biological threats; however, with the advent of personalized medicine, the DoD has also recognized the value of routine health-status monitoring and the availability of point-of-care (POC) diagnostics in addition to environmental monitoring. In fact, DARPA has numerous programs aimed at monitoring biological systems to allow for rapid intervention. However, despite decades of investment, no commercial instruments are available that perform nucleic acid processing at the point of need. To fill this gap, SRI has developed and we disclose here a portable, integrated, rapidly reconfigurable and automated biodetection system that performs "sample-in to answer-out" analysis.

SUMMARY OF THE INVENTION

The invention provides devices, systems and methods for the parallel detection of a set of distinct nucleic acid sequences via multiple sequence amplification and simultaneous hybridization readout.

In one aspect, the invention provides an automated nucleic acid analysis system comprising in microfluidic connection sample lysis, purification, PCR and detection modules configured to detect in parallel distinct nucleic acid sequences via multiple sequence amplification and simultaneous microarray hybridization readout.

In embodiments the invention provides the system wherein:

the detection module comprises microarray detection optics comprising a microarray scanner employing evanescent wave excitation;

the detection module comprise an automated hybridization processor configured to provide multiple stringencies via temperature; and/or the PCR module is configured to perform reverse transcription and PCR in a single reaction.

In embodiments the invention provides the system wherein comprising an integrated microfluidics card comprising the modules and an analyzer comprising a receptacle configured to receive the card, operators configured to operate the card, and a controller configured to electronically control the operators, the operators comprising fluidic actuators, PCR thermal cycler, and automated hybridization processor and microarray detection optics.

In embodiments the invention provides the system further comprising a reagent module configured to contain and deliver reagents to the lysis, purification, PCR and detection modules.

In embodiments the invention provides the system wherein that is:

portable: less than 1000 m$^3$ and less than 10 lbs;

rapid: analysis in less than 120 minutes;

multiplex: simultaneous analysis of more than 50 target sequences; and/or automated: requiring no user intervention between sample introduction and result display.

In embodiments the invention provides the system wherein:

the sample comprises protein analytes and the system is further configured to tag the protein analytes with tags comprising the nucleic acid sequences;

anchored probes define the sequences by their spatial locations;

the amplification is effected by a number of primers pairs less than the number of sequences being analyzed;

the distinct nucleic acid sequences are of multiple species/organisms;

the PCR module comprises a metallic (e.g. aluminum) PCR reaction chamber;

the microfluidic connection comprises a breathable membrane configured for bubble removal, wherein the breathable membrane is underneath the channel layer, so the entire channel can be exposed to atmospheric pressure (in a particular embodiment, this membrane spans the card because it is easier to manufacture it as a layer than individual pieces, though it is only functional under the channel layers);

amplification is fully contained in the consumable (no open tubes, etc.); and/or detection is based on probe sets rather than primer sets (easier to build new tests).

In embodiments the invention provides the system configured to:

amplify in a single vessel (no sample splitting);

receive and process analyte samples of blood, saliva, GI samples, urine, wound swabs, spinal tap, nasal swabs, veterinary and agricultural sources;

receive samples via a specimen collection tool or transport media;

process sample volumes between 1-100 ul;

be modular (modules can be interchanged to support different applications);

be capable of metering (done by channel dimensions and bubble removal); and/or be one directional and self-sealing (prevents sample cross contamination).

In embodiments the invention provides the system comprising an integrated microfluidics card comprising the modules and an analyzer comprising a housing (box) and within the housing receptacle configured to receive the card, wherein the analyzer:

engages the card to perform the lysis, purification, PCT (amplification and labeling), and detection;

interacts with the sample via pressure (e.g. sample transport), magnetic fields (e.g. sample mixing), temperature (e.g. amplification, stringency, hybridization) and/or light (e.g. hybridization detection); and/or performs the detection by coupling an evanescant wave with the sample to observe hybridizations in real time and/or determining kinetics and possible base-pair mismatch which result in sequence information.

In embodiments the invention provides the system comprising an integrated microfluidics card (cartridge) comprising the modules, wherein the card is configured:

to be specific to disease type (ex. respiratory illnesses);

to be specific to patient type (ex. pediatric);

to be specific to pathogen type (ex. biowarfare agents);

to be specific to individual (ex. pharmacogenomics);

to contain unique identifiers for paient-specific information;

for one-time use to maintain sterility and minimize cross-contamination;

to be produced using roll-to-roll manufacturing steps; and/or from a polycarbonate chassis, metallic foil PCR chambers, acrylic components, breathable membrane materials, and/or polyurethane seals.

In embodiments the invention provides the system functionally integrated with a microfluidic particles sorter, such as a fluorescence-activated cell sorter (FACS), configured to provide hydrodynamic and/or inertial focusing for particle or cell alignment and comprising microscale electroactive polymer (EAP) actuators configured for sorting.

The EAP µ-sorter may be functionally integrated with or incorporated as particle-concentration/sorting module of the iMFC system, and configured to allow the system to increase the operation envelope by either concentrating a dilute particle concentration in a large volume (e.g., bacteria present in environmental samples at a few cells per ml) or sorting out select cells from a background of many cells (e.g., activated T cells from a population of peripheral blood mononuclear cells. In addition, the microscale electroactive polymer actuators are suitable for alternative applications beyond sorting, including cell trapping, fluid mixing and pumping, and hence may be provided, configured and/or operated independent of the subject automated nucleic acid analysis systems.

The invention also provides methods of using the disclosed systems to detect in parallel distinct analyte nucleic acid sequences via multiple sequence amplification and simultaneous microarray hybridization readout.

In another aspect the invention provides a high performance microfluidic electroactive polymer (µEAP) actuator configured about a flow channel wherein a voltage pulse applied to the actuator induces the actuator to create across the flow channel a transient cross flow that deflects targeted particles within the flow channel onto a new pathline, wherein the actuator comprises a dead-end fluid chamber in which one or more surfaces (e.g. wall, floor, ceiling) of the chamber comprises an electrode covered with an EAP layer of dielectric elastomer.

A single uEAP actuator may be paired with a compliant chamber (i.e., "bellows") that accepts the fluid jet driven by the actuator. This configuration only requires one active actuator, but it still allows the generation of a cross flow. The compliant chamber could just be one of the actuators without an electrical connection, or it could be a chamber with a different geometry, as we use for the multi-channel/stage sorters.

While exemplified primarily with solid electrodes (e.g indium tin oxide (ITO) electrode on a glass slide), the electrode could also or alternatively comprise a fluid, such as a conductive fluid in an adjacent channel.

In another aspect the invention provides a plurality of such actuators configured about the flow channel and out of phase with each other, wherein a voltage pulse applied to the actuators induces the actuators to create across the flow channel a transient cross flow that deflects targeted particles within the flow channel onto a new pathline, wherein each actuator comprises a dead-end fluid chamber in which a surface of the chamber is an electrode covered with an EAP layer of dielectric elastomer.

In another aspect the plurality is a pair of such actuators configured 180° out of phase with each other.

In embodiments:

a plurality of surfaces of the chamber(s) comprise an electrode covered with an EAP layer of dielectric elastomer;

the flow channel is configured to provide a combination of hydrodynamic focusing for horizontal alignment and inertial focusing for vertical alignment of the particles;

the new pathline leads to a sort outlet;

the flow channel comprises a sample input channel and sorted and unsorted output channels and the new pathline leads to the sorted output channel;

the flow channel is configured for fluorescence detection, wherein upon detection of a targeted particle, the voltage pulse is applied to the µEAP actuators;

the EAP layer is 1-50 (or 2-25, or 5-15 µm thick);

the elastomer is silicone;

the actuator(s) are configured to provide parallel sorting in a multi-channel device;

the actuator(s) are configured to provide multi-stage serial sorting into multiple outlets; and/or the actuator(s) are functionally integrated in a label-activated particle sorter.

The invention also provides methods of making and using the actuators, such as comprising the step of applying a voltage pulse to induce the actuator(s) to create across the flow channel a transient cross flow that deflects targeted particles within the flow channel onto a new pathline.

The invention specifically provides all combinations of the recited embodiments, as if each had been laboriously individually set forth.

BRIEF DESCRIPTION OF THE FIGURES

FIGS. 5A and 5B: Valve control mechanics to control flow.

DETAILED DESCRIPTION OF PARTICULAR EMBODIMENTS AND EXAMPLES THEREOF

Our invention provides a portable, inexpensive molecular diagnostic system capable of producing results with no human intervention—human intervention is only needed to input the sample and to read the results. The results are also produced very quickly due to the various techniques described above. The system includes a method to interface with a disposable member, called the iMFC. The methods and the systems allow the iMFC to be configured easily to run different types of tests without the need to modify the underlying hardware. Finally, the card itself is modular, readily modifiable for running different types of tests.

In an aspect the invention provides a self-contained system that can take a sample as the input, perform molecular diagnostic steps and display the result of the diagnostic tests. Typically, the steps include (i) extraction and purification, e.g. where the DNA sample is extracted from the input sample, which may be blood, tissue, urine, saliva or other bodily fluid; (ii) amplification and labeling, e.g. where a specific sequence of the sample is amplified; (iii) hybridization; (iv) stringency wash to remove unnecessary molecules that are bound to the target sequence and (v) readout where the identification step is completed and the specific sequences are identified. The system generally comprises a disposable member called the integrated microfluidic card (iMFC) and a non-disposable base unit. The integrated microfluidic card may be coupled to the base unit through an interface scheme. Fluid flow in the iMFC may be achieved by controlling valves that form the part of the structure of the card. Each card may be designed to detect and identify a certain set of biological markers.

In embodiments, the steps between sample input and readout are carried out without needing any human intervention, the system does not split the sample, the system is able to identify at least 1,000 targets, the system can identify over 50 targets per run and/or implements all the testing steps in a single system, and/or using real-time hybridization the system is able to predict results before hybridization is complete and can provide information about target concentration.

Figure 1:
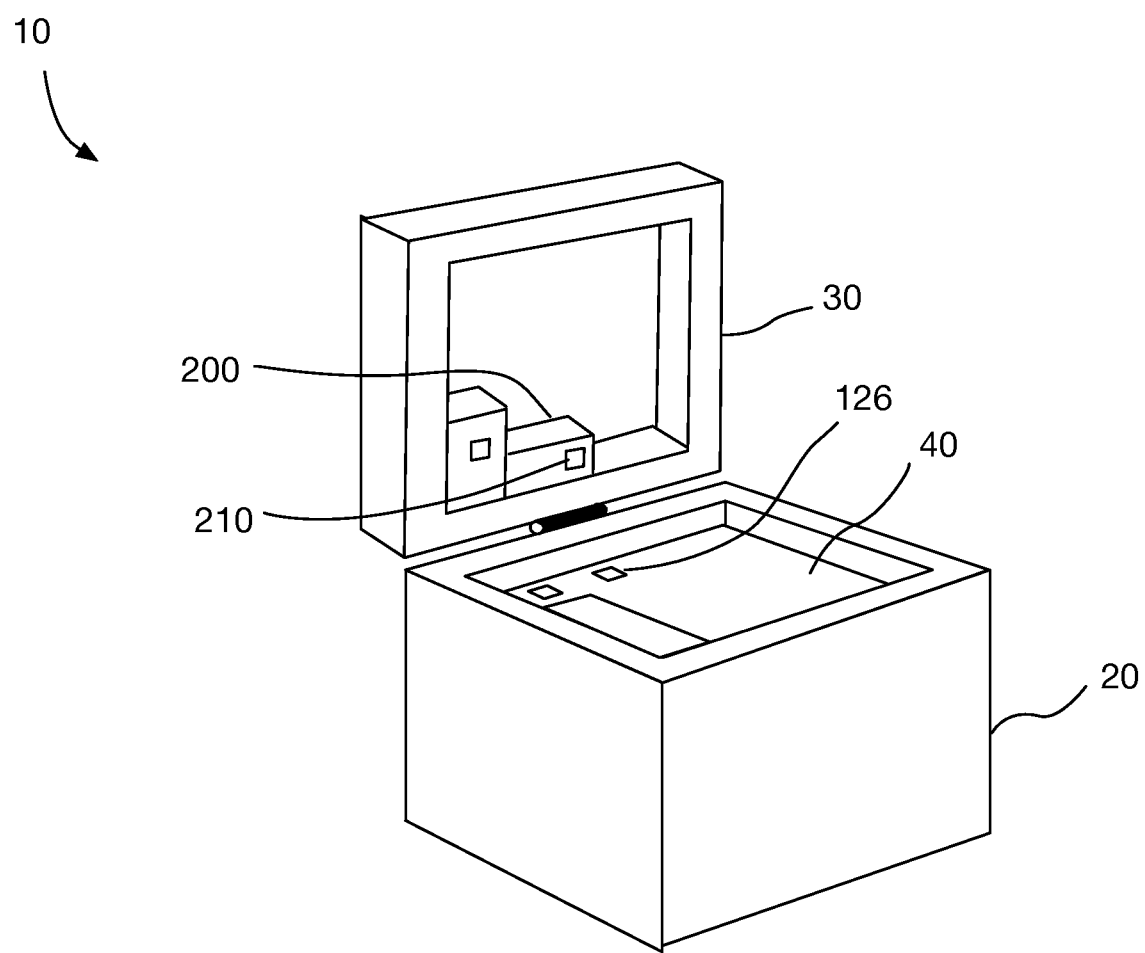
FIG. 1: A physical configuration of a molecular diagnostic system.

FIG. 1 shows the overall system 10. The system comprises a unit base 20, a unit lid 30, and a disposable integrated microfluidic card (iMFC) 40. The design of the card is modular such that it can be customized for accepting sample inputs in various forms including but not limited to blood drops, nasal swabs, sputum etc., or customized for conducting different tests. In general, the testing process begins by first choosing an appropriate card, placing the sample in the input chamber of the card, placing the card in the unit base, shutting the lid and choosing the appropriate software to run. Once the testing process commences, no human intervention is required. The results may be displayed on a screen that may be integrated as part of the system or they may be transmitted to an external device such as a computer or a smart phone. After the tests are concluded, the card may be disposed of and a different one may be chosen for the next test. The order of these steps may be changed as needed.

Disposable Integrated Microfluidic Card.

Figure 2A:
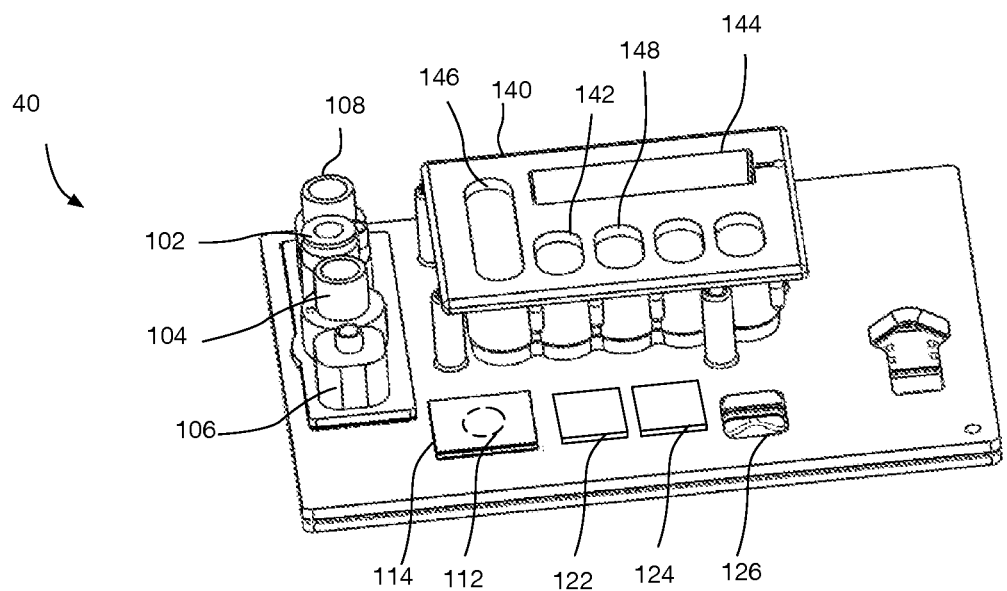
FIGS. 2A and B: A iMGC card.
Figure 2B:
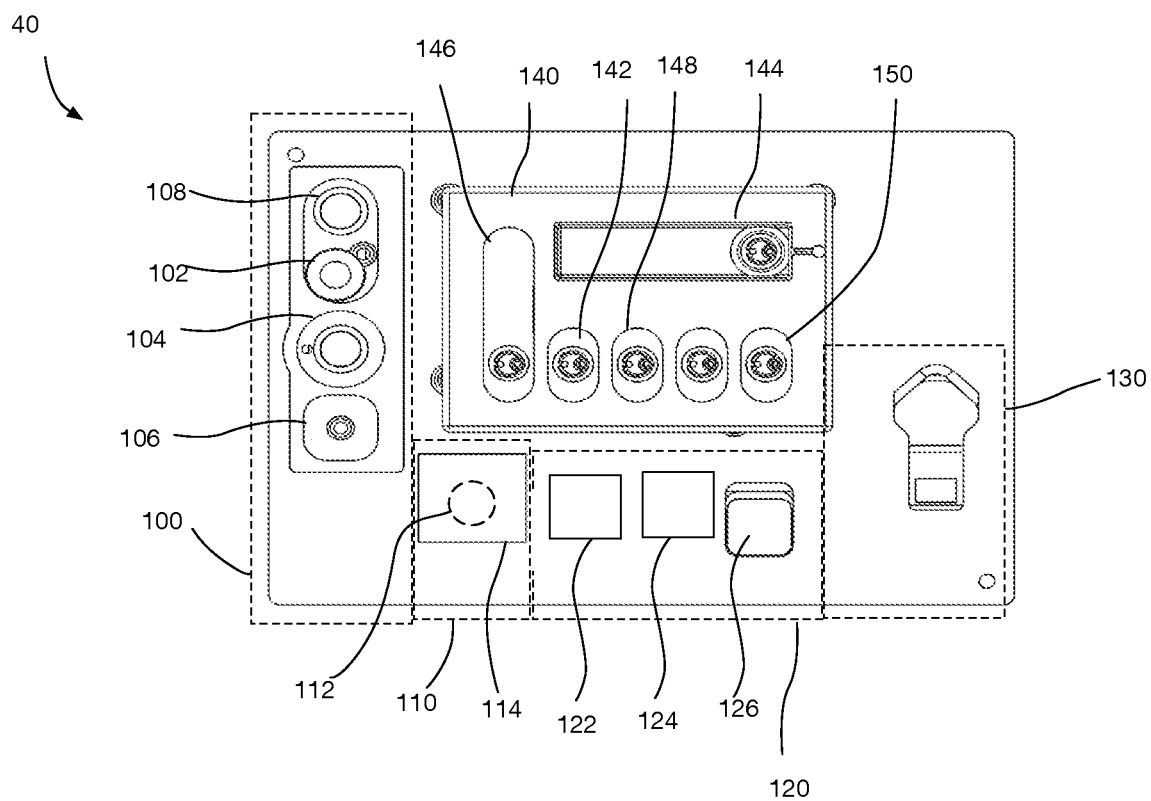
FIG. 2C: An input module for a nasal swab.
FIG. 2D: A TECs are arrangement.
FIG. 2E: A section of the iMFC card around the PCR and the detection processing blocks.
FIG. 2F: A glass substrate with the detection well, the gratings and the chrome.
FIG. 2G: A side view of the glass substrate illustrating how light is coupled into the glass substrate.
FIG. 2H: A side view of the glass substrate illustrating how light travels through total internal reflection within the glass substrate.
FIG. 2I: An arrangement of the TEC and the camera system in relation to the microarray.

The card generally combines multiple functions, such as lysis, purification, amplification, labeling and detection—in one card. In typical on-market systems, these functions are accomplished with multiple instruments. We achieved consolidation of the functions by integrating numerous techniques and features for bubble removal and accurate metering, integration of the evanescent field imaging system, choice of reactants and chemistries at various steps and rapid amplification and real time hybridization, etc. Consolidation of the multiple functions into one card may allow for CLIA waiver. FIG. 2A illustrates a perspective view of the card and FIG. 2B illustrates a plan view. FIG. 2B also illustrates the areas (shown in dashed lines) where various functions may occur within the card. For example, block 100 may be the lysis block, block 110 may be the purification block, block 120 may be where the polymerase chain reaction (PCR) process occurs and block 130 may be where the detection occurs. Fluid containing the test sample flows from one block to another block in the order described above through channels that are incorporated within the card. The flow of liquids through these channels from one block to another is controlled by micro-valves that may be open or shut depending on the pressure imposed at the valves.

Lysis Block.

Figure 2C:
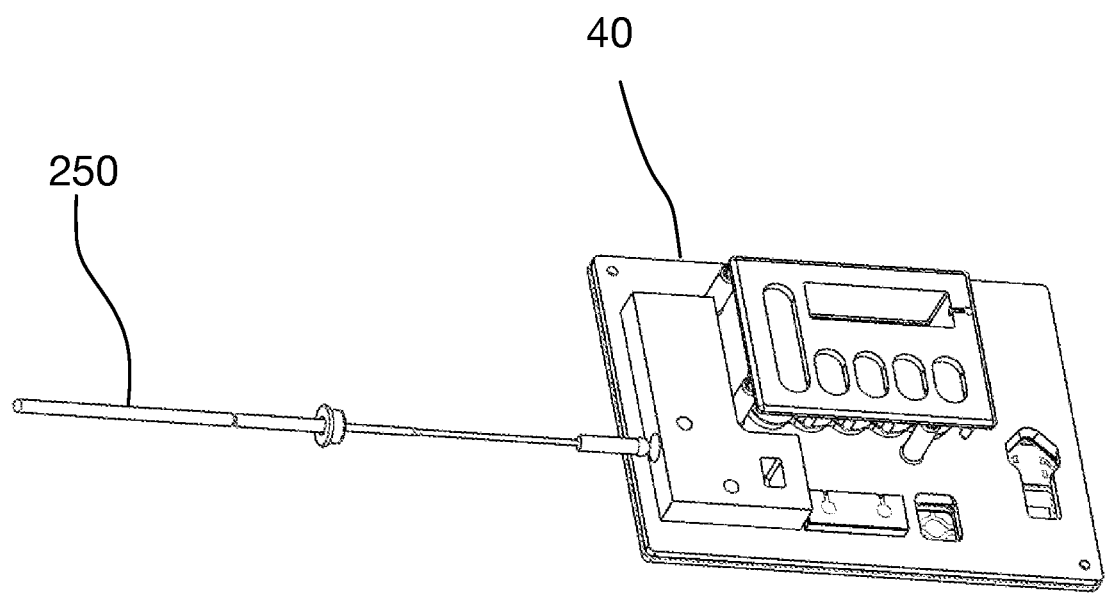

Sample input may also occur within the lysis block, FIGS. 2A and 2B, block 100. Various methods may be used to input the samples such as using blood drops and nasal swabs. In one embodiment the card directly accepts the tool used to collect the sample. Typically, in on-market systems, the tool used to collect the sample does not directly interface with the testing instrument. By allowing direct interface of the tool with the test instrument, a source of contamination and user error may be eliminated. Since the card is modular, the lysis block may be modified to accept various methods of input. Referring to FIGS. 2A and 2B, member 102 may be an input chamber that accepts a sample such as a drop of blood. FIG. 2C illustrates an advantage of modularity, wherein the lysis block is configured to accept a nasal swab 250 as an input. For both these cases of using a blood drop or a nasal swab, the underlying design of the card 40 may be the same; only the input module may be different.

In addition to accommodating various methods of input, the lysis modules may be configured to carry out different types of lysis, such as mechanical, chemical or other types. In reference to FIGS. 2A and 2B, the lysis block is illustrated as having a bead beater 104, which comprises a bead chamber filled with beads and a small motor mounted atop the bead chamber which forces the beads to collide into one another. Cells located between the colliding beads lyse, freeing up its contents into the lysis buffer solution—an example of mechanical lysis. Other modules may be configured to perform other types of lysis, and these modules may have different or fewer chambers or sub-modules than shown in FIGS. 2A and 2B. For example a module capable of performing chemical lysis may have, instead of the bead beater, another chamber where a chemical (perhaps stored in the reagent block and piped into the chamber at an appropriate time) may be mixed with the lysis buffer solution containing the sample. Thus different types of lysis may be accommodated with the same basic design of the card.

To start the process of lysis, a lysis buffer solution stored in the lysis buffer well 142 in the reagent block 140 is piped into the chamber 108. The method to control the fluid flow within the card may be achieved through controlling microvalves. Chamber 108 may have a gas permeable vent at the top such that as a liquid touches the vent, it is air-locked due to the pressure difference between the chamber and atmosphere, letting the air in the chamber out while it is being filled. This vent may be made of various materials such as Teflon. When chamber 108 is filled, a valve between it and input chamber 102 may be opened, letting the buffer solution mix with the input sample. Once the lysis buffer and the input sample are mixed, another valve between the input chamber 102 and the bead beater 104 may be opened to let the mixture into the bead beater. The motor atop the bead beater is then turned on for a specific amount of time after which, the valve between the bead beater 104 and chamber 106 is opened and the solution now flows into chamber 106. Chamber 106 may be pre-filled with a reagent such as guanidine-hydrochloride where it mixes with the lysed solution. After mixing with the reagent is complete, the valve between the chamber 106 and purification block 110 may be opened to direct this mixture into the purification block. The guanidine-hydrochloride enables the DNA in the sample to bind with a silica based structure in the purification block thus helping in the process of purification.

The configurations to provide capability to do different types of lysis, to accept various methods of input and to accept the actual tool for the input method are advantageous characteristics, which may be synergistically combined in device 10.

Purification Block.

Figure 3:
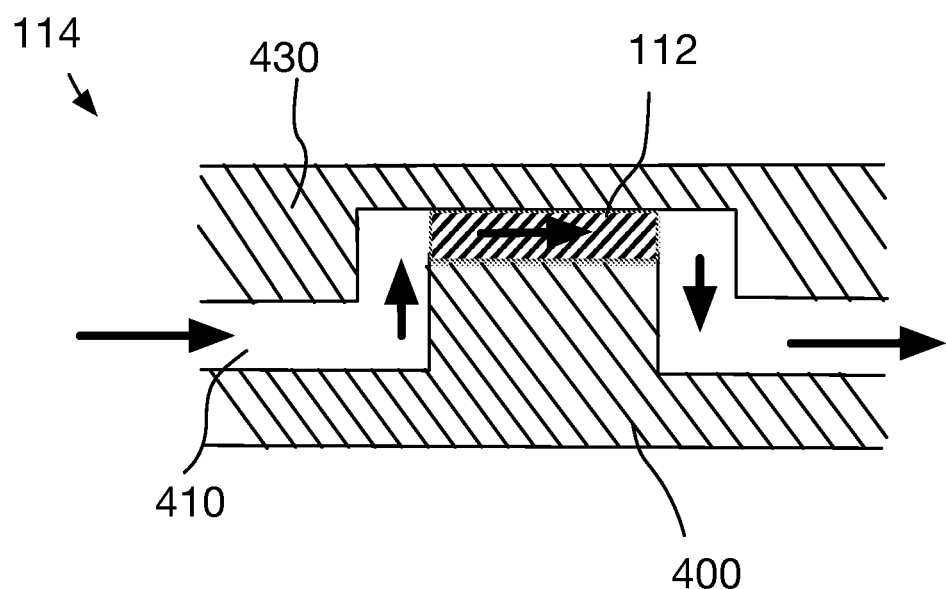
FIG. 3: Mechanics to bind nucleic acid to a silica frit.

When the valve between chamber 106 and the purification block is opened, the solution comes in contact with a silica frit that is placed within the purification block. The frit and the structure that holds the frit, are enumerated by 112 and 114 respectively in FIGS. 2A and 2B. The flow of the solution across the frit is illustrated in FIG. 3. This figure shows a section of the card around the silica frit 112. The silica frit may be in the form of a mesh sitting in a channel 410 that may be sandwiched between a base layer 400 and a top-cap layer 430. The base layer, the top-cap layer form part of the structure 114 that holds the frit. The arrows indicate the flow of fluids within the channel 410. The solution containing the nucleic acid in the solution from chamber 106 containing the guanidine-hydrochloride will bind to the frit and flow in the direction of the arrows. The flow of the solution after it flows past the frit may be directed by micro-valves to either flow into a residue chamber or may be directed for further processing. Hence the DNA in the solution binds to the frit but other components of the solution such as proteins and lipids that do not bind to the frit flow past the frit and may be directed through channels into a residue collection chamber 144. After the DNA binding step, a washing step is performed. Ethanol contained in the ethanol reservoir 146 is allowed to flow over the frit to perform the washing step to wash away unwanted components of the lysate that may still be bound to DNA. The ethanol is then allowed to dry. The next step in the purification process is to let the elution buffer stored in the elution buffer well 148, wash over the frit. This step allows the nucleic acid to uncouple from the frit. The solution is now allowed to enter the PCR process block 120. At this step, the valve to the further processing step (PCR process) is opened but the valve to the residue chamber is shut.

PCR Block.

After the purification block polymerase chain reaction (PCR) may be implemented, preferably with system adaptations such as described below. PCR is carried out in the PCR block enumerated by 120, and may be carried out in multiple steps as shown in FIGS. 2A and 2B. After the elution wash from the purification step is completed, the purified solution containing the nucleic acid is allowed to flow into the PCR master mix chamber 122. Here, the purified solution is mixed with lyophilized (freeze-dried) enzymes that are carried within the structure of the master mix chamber. These enzymes are needed for the amplification step that occurs further down in the processing chain. The master mix chamber may comprise a well where the volume of the solution filling the well may be controlled, allowing a precise volume of the solution and avoiding or eliminating air bubbles. The precise volume in the various stages of processing results in accuracy of the results.

After mixing with the enzymes is completed, the solution is allowed to flow into PCR primer chamber 124, where the solution mixes with the lyophilized primers. The primer chamber also may be a well where the volume is controlled precisely in addition to avoiding or eliminating air bubbles entrapped in the solution. The separation of the steps involving the mixing with the master mix and the primers may be advantageous in some situations as this allows the use of commonly available master mix modules and reduce the overall cost of the device. In addition, the separation into the two steps also allows rapid deployment of kits to test for emerging threats for example as it may be possible to make multiple cards with different primers which may be used to check for the presence of different target molecules. The process of lyophylization of the primer (oligonucleotides) is quick and simple and may be carried out in a laboratory external to the device 10. Thus by separating out the two mixing steps, the card may be modified to test for different substances, though the mixing process may also be performed in one step if preferred.

After mixing with the primers is complete, the solution then flows to the PCR chamber 126. In a departure from traditional on-market approaches where a PCR chamber may be made of non-metallic materials, the PCR chamber in the iMFC card may be made of a passivated metal such as but not limited to aluminum. The use of metal and particularly of aluminum is advantageous as it allows rapid control of temperature of the solution within the aluminum chamber. This rapid control is achieved by having the top and the bottom of the aluminum chamber to be in close contact with thermoelectric coolers (TECs). Close contact between the PCR chamber and the TECs is obtained by locating two TECs above and below the PCR chamber. The TEC above the PCR chamber is placed on lid 30 of the device 10 (FIG.

Figure 2D:
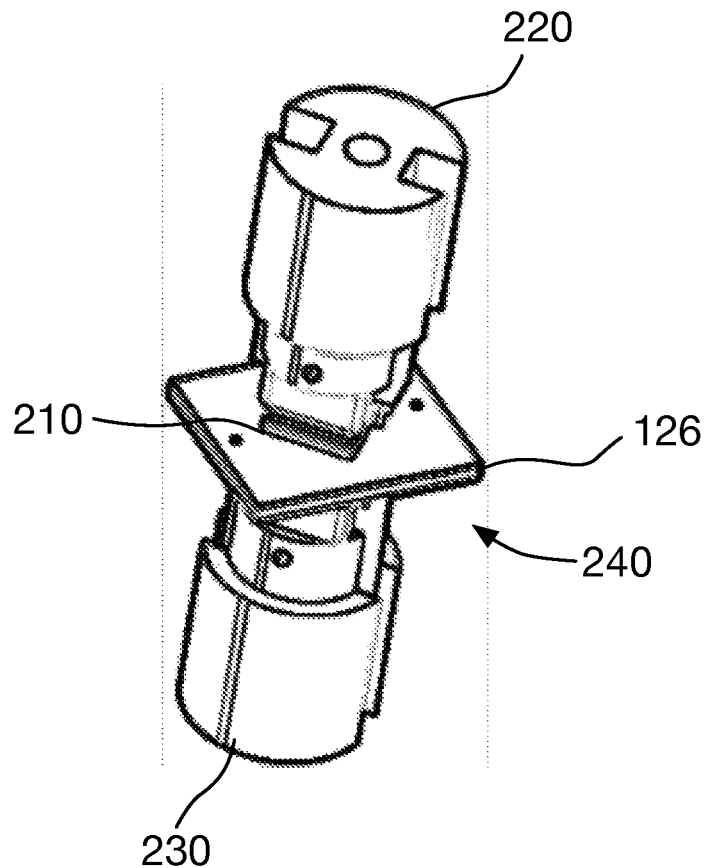

1) within a TEC housing unit 200. The shape of the face of the TEC 210 and the shape of the PCR chamber 126 are made to match such that when the lid is shut, the TEC face may be located directly over the top surface of the PCR chamber. The TEC below the PCR chamber is simply placed within the unit base 20. FIG. 2D illustrates how the PCR chamber may be sandwiched between two TECs 220 (with TEC face 210) and 230 (with TEC face 240 which is not visible in the figure). Thus this arrangement of the TECs and the use of the aluminum PCR chamber enable rapid temperature cycling of the PCR mixture. It has been found through measurements that this combination allows a temperature ramp of >15° C./s with accuracy of ±1° C. This configuration then contributes directly to the shortening of the time between the sample input and result output. In addition to the advantage obtained in the rapid temperature control of the solution due to the use of the passivated aluminum, yet another advantage may be realized in that lower amount of energy is needed to heat and cool the solution compared to what would have been required if non-metallic materials were to be used for the PCR chamber. The lower amount of energy translates directly to needing lower overall power to run the device, enabling optional battery operation and field portability.

Figure 2E:
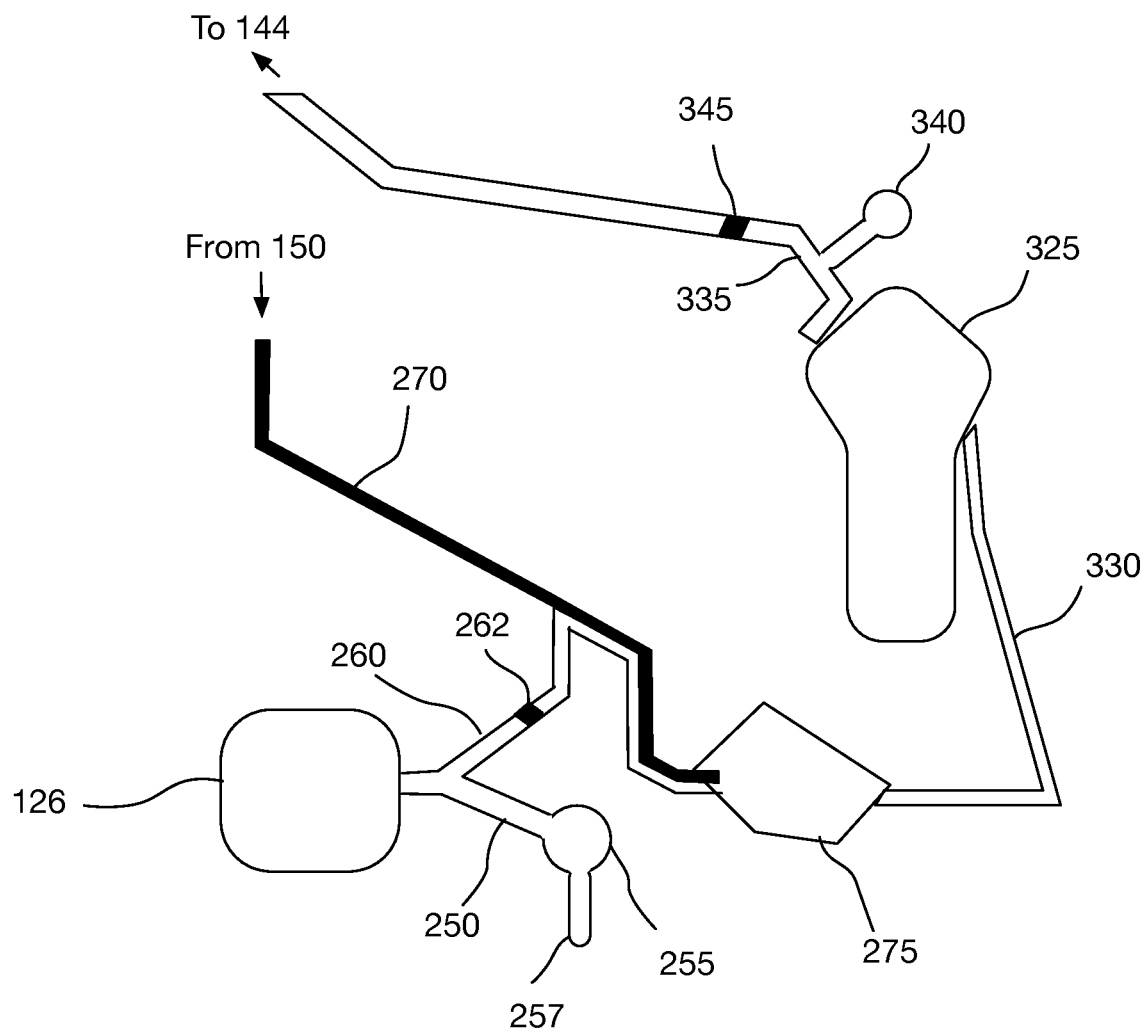

Another aspect of the PCR chamber 126 is now explained with referenced to FIG. 2E, which shows sections of the card around the PCR chamber and the detection block 130. To preserve the concentrations of the solution, trapped air should be avoided or minimized within the PCR chamber while the PCR process occurs. The top and the bottom sections PCR chamber, as described may be made of passivated aluminum; hence a breathable membrane may not used here. Hence an outlet channel 250 from the PCR chamber is provided that leads to reservoir 255 that in turn opens to the atmosphere through another channel 257. Hence as the chamber 126 is filling with solution, air is pushed out and bled to atmosphere. A valve in channel 260 may be shut while the chamber 126 is filling. During the filling process, channel 250 and reservoir 255 may also fill with solution, which prevents air from coming back into the chamber 126. Also, as the solution is driven by a constant pressure of 6 psi, no backflow from the channel 250 or the reservoir 255 occurs. After the chamber is filled, the PCR process is commenced. At the end of the PCR process, the required target sequences are amplified and labeled for detection within the detection block.

Detection Block—General Description.

Figure 2F:
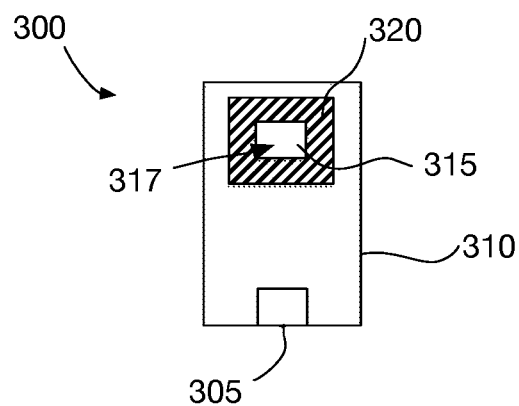

After the PCR process is complete, referring to FIG. 2E, valve 262 in channel 260 may be opened and the solution with the amplified components (amplicons) in the PCR chamber 126 may be flowed into a mix chamber 275. Here the solution is mixed with a hybridization buffer that may be stored in the hybridization buffer well 150 in the reagent block. The solution from the hybridization buffer is metered before it is allowed to mix with the PCR product. After the mixing process in the mix chamber 275 is complete, the solution is allowed to flow into the detection chamber 325 via channel 330. The detection chamber 325, the mix chamber 275, the channels which transport solutions in and out of the chambers all form part of the detection block 130 illustrated in FIG. 2B. Next, within the detection chamber, the PCR product mixed with the hybridization buffer may be allowed to flow over a DNA microarray. This occurs in the detection well 317 as seen in FIG. 2F, where the well holds the solution and the microarray 315 is placed at the bottom of the well. Thus with this configuration, the solutions is located on top of the microarray. FIG. 2F illustrates the arrangement of the DNA microarray 315 and explains how the light is coupled into the microarray as this light forms part of the optics system that is used to read the microarray. The DNA microarray may contain several probes arranged in a grid pattern over a glass substrate 310. Each probe may contain a strand of a DNA (or RNA) and is used to detect the presence of nucleotide sequences in the sample solution that are complementary to the sequence in the probe. As stated, these probes are located in a grid pattern on top of a glass substrate 310. Light is coupled into the glass substrate via gratings 305 that are etched within the glass.

Figure 2G:
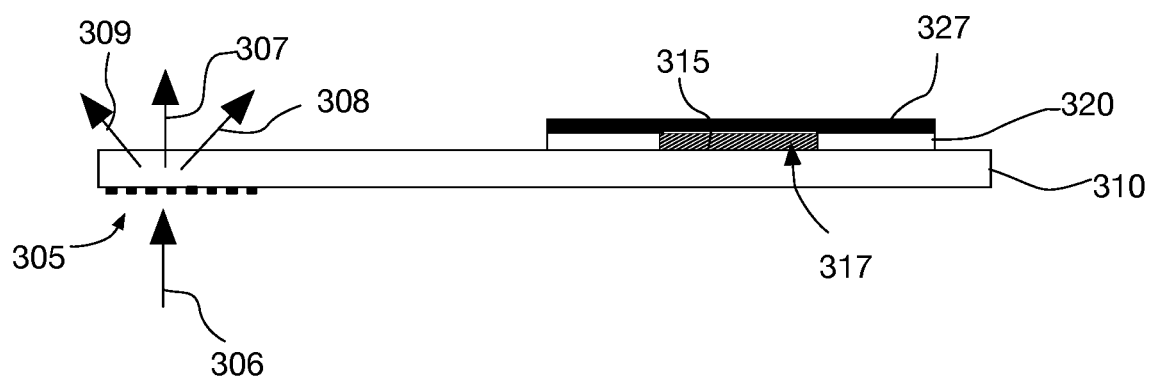
Figure 2H:
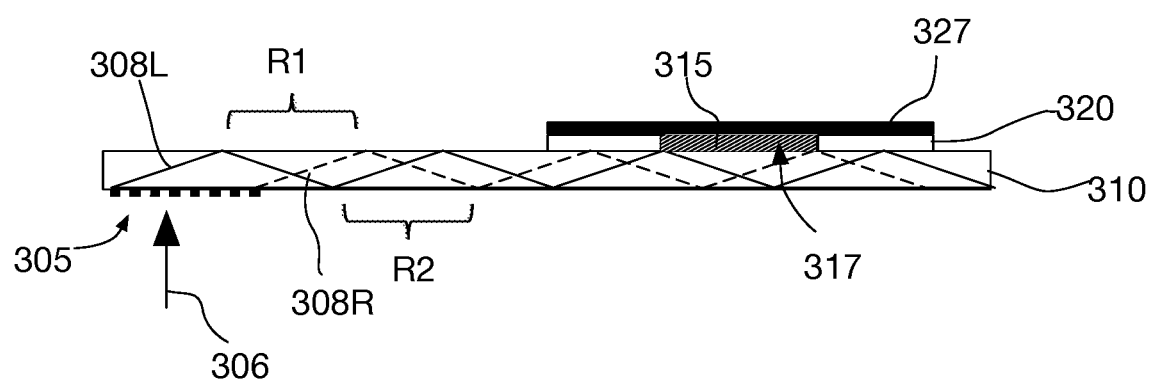
Figure 2I:
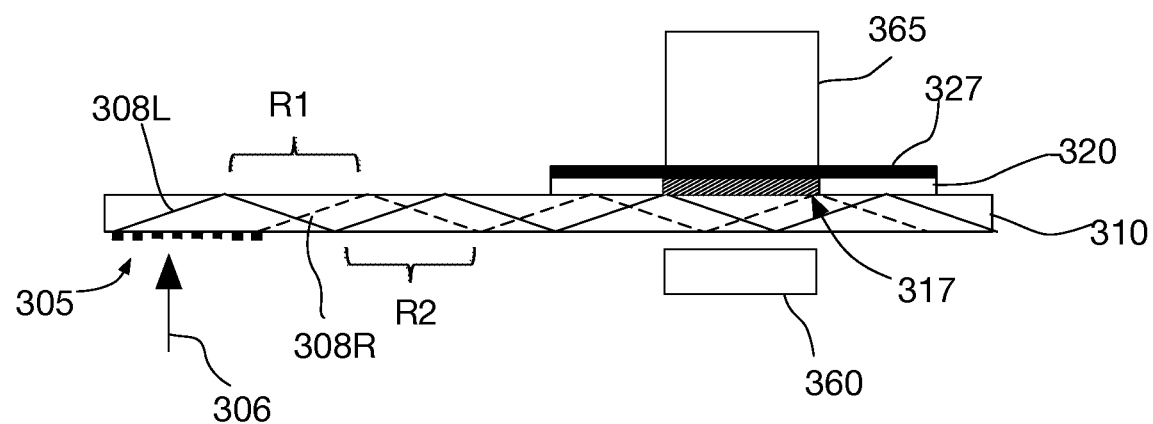

Referring to FIG. 2G, the gratings are illustrated along with an incident light 306. The incident light 306 may be at a specific wavelength. Due to the presence of the gratings, the incident light may travel in multiple directions; some light may be transmitted right through as shown by 307, some light may be transmitted at specific angles as shown by 308 and 309. Light may be transmitted at additional and steeper angles with respect to the light 307, but they are ignored in this disclosure as the intensity of the light at the steeper angles tends to be lower. The angles at which light is transmitted (for light not transmitted in a straight line) are determined by the well-known grating equation. The angle of light 308 and 309 may be adjusted by adjusting the wavelength of the incident light 306 and by the patterning of the gratings. Next, to couple light into the glass substrate, the process of total internal reflection is used. This concept is illustrated in FIG. 2H. In this figure, the light 307 that is transmitted straight through and light 309 transmitted at an angle is ignored. Light 308 is illustrated by a beam constrained by the size of the gratings 305. Thus the beam of light 308 is illustrated by a solid line 308L emanating from the left edge of the grating and by a dashed line 308R emanating from the right edge of the grating. The solid line and the dashed line are used to distinguish the two edges of the beam; no other difference is indicated. Depending on the angle of beam 308 and the indices of refraction of the glass substrate and of the surrounding environment (essentially air), total internal reflection may be set up at the top surface of the glass substrate region 1 marked as R1. This reflected light may reach the bottom surface of the glass substrate and may again be totally internally reflected at region 2 (marked as R2). Thus though total internal reflection, the light may be steered behind the detection well 317, below the microarray 315. As stated earlier, the microarray 315 is located at the bottom of the detection well 317. Now that the light is steered to the location of the microarray, another phenomenon called evanescent fields is made use of to excite the light sensitive molecules in the DNA microarray. It is well known in optics that at boundaries where total internal reflection occurs, an evanescent field is set up on the other side of the boundary. These evanescent fields are a near-field phenomena and the intensity drops exponentially further away from the boundary. However, very close to the boundary, the evanescent fields are able to excite the light sensitive molecules and since the solution in the detection well 317 is located at and near the boundary, the detection method of using evanescent fields becomes possible. Returning back to FIG. 2H, the detection well is seen to be placed within an enclosing layer 320; this enclosing layer is made of chrome. The chrome layer is also shown in FIG. 2F, surrounding the detection well on all four sides. The chrome is included as part of the design so that stray light from the immediate vicinity of the detection well is reduced or eliminated. The possibility of erroneous light is further removed by coupling a black plastic sheet 327 over the detection well. Materials other than plastic may be used as well.

The grating design and the subsequent angle of light 308, the thickness of the glass substrate, the index of refraction of the glass substrate, the distance between the grating and the detection well are parameters we have optimized for this device and provide synergistic functionality. In addition, the angle of light 308 may be selected so that it not only totally internally reflects from regions such as R1 and R2 (essentially from a glass-air boundary), but also from the glass-solution boundary in the detection well. The index of refraction of the solution in the detection well is approximately 1.33 while that of air is approximately 1. The grating pitch, grating material, and substrate index can be altered to use different wavelength laser light. In one example, a 633 nm wavelength light was used with a 150 nm silicon nitride grating at a 195 nm pitch on a 750 micrometer fused silica substrate. The light is coupled into the substrate with a 10° divergence. The distance between the grating and the microarray is chosen to such that the microarray is positioned at a distance corresponding to an integral number of total internal reflectance bounces. All parameters specified above may be adjusted as required. For example other wavelengths of light may be used which may then require a different grating spacing than specified above.

A TEC 365 may be placed over the detection well 317 to control the temperature of the solution. Finally a CCD camera 360 may be placed beneath the microarray so that a one to one image of the microarray may be formed on the camera detectors. The camera system takes photographs of the solution over the microarray. The photographs reveal the areas within the microarray that may be fluorescing. This information is used in the identification and detection process.

The invention exploits synergistic combinations of the described improvements and adaptations to implement the detection function.

Detection Block—Quality Control.

In addition to identifying the target sequences within the sample, the microarray may be used to also ensure that the steps (lysis, purification, mixing with the enzymes and the primers etc) occurred as desired. Markers may be added at each step and presence or absence of the markers may be tested optically within the microarray. Thus by analyzing the presence or absence of markers, quality control may be achieved to identify if and where the tests may not have run appropriately.

Detection Block—Pan-Amplification.

The device 10 may be used to avoid sample splitting to test for various nucleic acid sequences. Sample splitting is commonly used in on-market systems; it requires that the sample be divided into multiple samples where each divided sample may be tested for a certain sequence. Since the original sample is split into multiple samples, this method reduces the detection limit by a factor equal to the number of sample splits. Instead of using sample splitting, we implement a process called pan-amplification, by which the variations within a species of bacteria or virus may be identified without splitting the sample. This type of testing becomes possible because some sections of the DNA of the variants within a species may be same or similar. Knowing that certain sequences are present, the primers may then be designed to identify the variants.

Typically PCR is limited to about 20 different primer sets, which limits the number of targets that the on market systems can detect. Our system overcomes the limitation by pan-amplification, wherein the PCR primer set targets DNA sequences that are common across many organisms, while the region in between the primers contains DNA sequences that are highly variable between organisms. The pan amplification approach allows for differentiation of the sample type at the microarray where high multiplexing is possible. For example conserved regions of coronavirus polymerase gene allow for amplification of 6 different coronavirus serotypes with a single primer set, while each serotype is distinguishable on the microarray by analyzing the variable region amplified between the primer sets.

One advantage of the pan-amplification is that fewer primers are needed than a typical on-market device doing PCR. Use of more than 20 primers can lead to a phenomenon called "primer dimer" where primer molecules hybridize to each other due to the strings of the complementary bases in the primers, whereas our pan-amplification process allows the use of fewer primers hence resulting in an advantageous configuration.

Detection Block—Real Time Hybridization.

In another advantageous configuration, a real time hybridization approach is implemented within device 10 that results in shortening the time between sample input and results output. In typical on-market approaches, hybridization is allowed to continue until stable concentrations of the sample or samples being tested are achieved. In contrast, in device 10, a real time approach is implemented where the concentration of the sample or samples is estimated repeatedly during the time the concentration of the sample or samples may be rising soon after the start of the hybridization. This technique is based on the observation that the strength of the signal from the CCD camera may be related to the concentration according to the kinetic curve equation, supra. Using the kinetic model, the fluorescence signal increase with respect to time may be monitored. This signal may be modeled or fitted as an exponential from which a time constant may be estimated. With an estimate of the time constant, the analyte concentration may be estimated.

Detection Block—Use of Multistage Temperature Control.

In typical on-market hybridization procedures, after the hybridization is complete, a stringency wash is performed so that unbound probes may be washed off. Typically, stringency washes are done by changing the salt concentration, however in device 10, a similar effect may be achieved by changing the temperature of the sample using the TECs while maintaining a constant salt concentration. Hence after hybridization is complete and an initial set of pictures are takes, the temperature of the TECs may be increased so that some of the unbound molecules may be removed. This allows for an advantageous way to perform a check on the results as changing the temperature of the solution is easier than changing the salt concentrations of the hybridization buffer.

Volume Control.

Testing procedure require accurate volume, which may be disrupted by air bubbles present in a fill chamber. In typical on-market systems, various devices such as peristaltic pumps are used, but the addition of these devices increases the cost and complexity of the device. Our device provides volume control that achieves high accuracy and precision (preferably 10% or less) and is inexpensive to implement.

Figure 4:
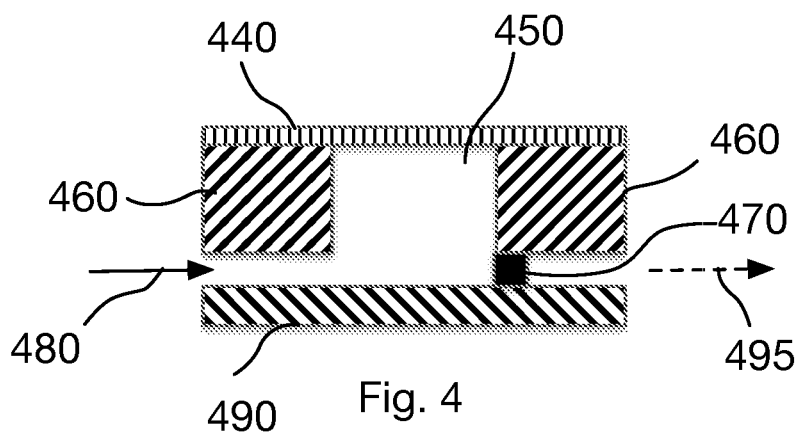
FIG. 4: Volume control with a breathable membrane.

FIG. 4 illustrates a fill chamber 450 in cross-section, along with the structures around the fill chamber. The fill chamber may be located on top of a base layer 490. The sides of the chamber are indicated by 460. Fluid may enter the chamber along arrow 480. The outlet of the fill chamber is marked by a dashed arrow 495. Member 470 may be a valve; if it is shut, no flow occurs along dashed arrow 495. A breathable membrane 440 may be mounted on top of the fill chamber as illustrated. With the valve closed, fluid may flow in the direction of 480, into the fill chamber 450. The breathable membrane may let the trapped air out and as the fill chamber fills, all the air is forced out. The breathable membrane does not let any air back in due to the pressure differential between the chamber and the atmosphere; thus with the valve 470 closed, a precise quantity of fluid may be collected within the fill chamber. The accuracy of the volume within the fill chamber may be determined by the accuracy of the dimensions of the chamber, and he dimensions of the chamber may be controlled using well-known techniques such as but not limited to machining and etching. The breathable membrane may be made of materials such as but not limited to microporous polypropylene. Thus with a combination of the precisely made chambers and the breathable membranes, accurate and precise volume control may be achieved.

The fill chambers along with the membranes are located in various locations within the iMFC card. Thus for example, fill chambers with breathable membrane may be used for the PCR master mix chamber 122 and the PCR primer chamber 124. In these two locations in particular, the lyophilized compounds may be located as a pellet within the chamber; thus the rehydration process within these chambers may occur in a volume controlled environment.

Valve Control.

FIGS. 5A and B illustrate how the valves and flow of fluid may be controlled within the iMFC card, including a fluid flow channel 520 and an air flow channel 540, and a flexible membrane 530. FIG. 5A shows two additional arrows 550 to indicate fluids may flow through the fluid flow channel 520. The fluid may be pumped through the system at a certain pressure such as 6 psi. If the membrane 530 is not deformed as illustrated in FIG. 5A, then channel 520 may allow free flow of fluids. However if a higher pressure such as 18 psi is applied to the air flow channel, the membrane may deform as illustrated in FIG. 5B, which effectively stops the flow through the channel 520. Thus by controlling the pressure on either side of a membrane flow through flow channels may be controlled. The pneumatic system that applied the differential pressure is described below.

iMFC Layers.

The iMFC card, as stated above, may be disposable and may constructed of inexpensive materials such as polycarbonate, acrylic, and polyethylene terephthalate. The card may be thought of as a "mother board" where different modules may be accommodated, such as where the card may be designed to have various different types of input modules to accommodate different methods of input. Not only can the card accommodate various modules, but the channel configuration may also be amended to accommodate different diagnostic tests or to add or subtract steps from a diagnostic test. Thus each card may be designed to accommodate a specific test or a set of tests, without needing to make changes to the underlying hardware. Each card may be made of one or multiple layers. One of the main functions of the card is to route fluids from one place to another at the appropriate time, through a system of fluid flow channels and air flow channels built into the card. Other functions include but are not limited to metering the flow and proving a temperature controlled environment.

Figure 6:
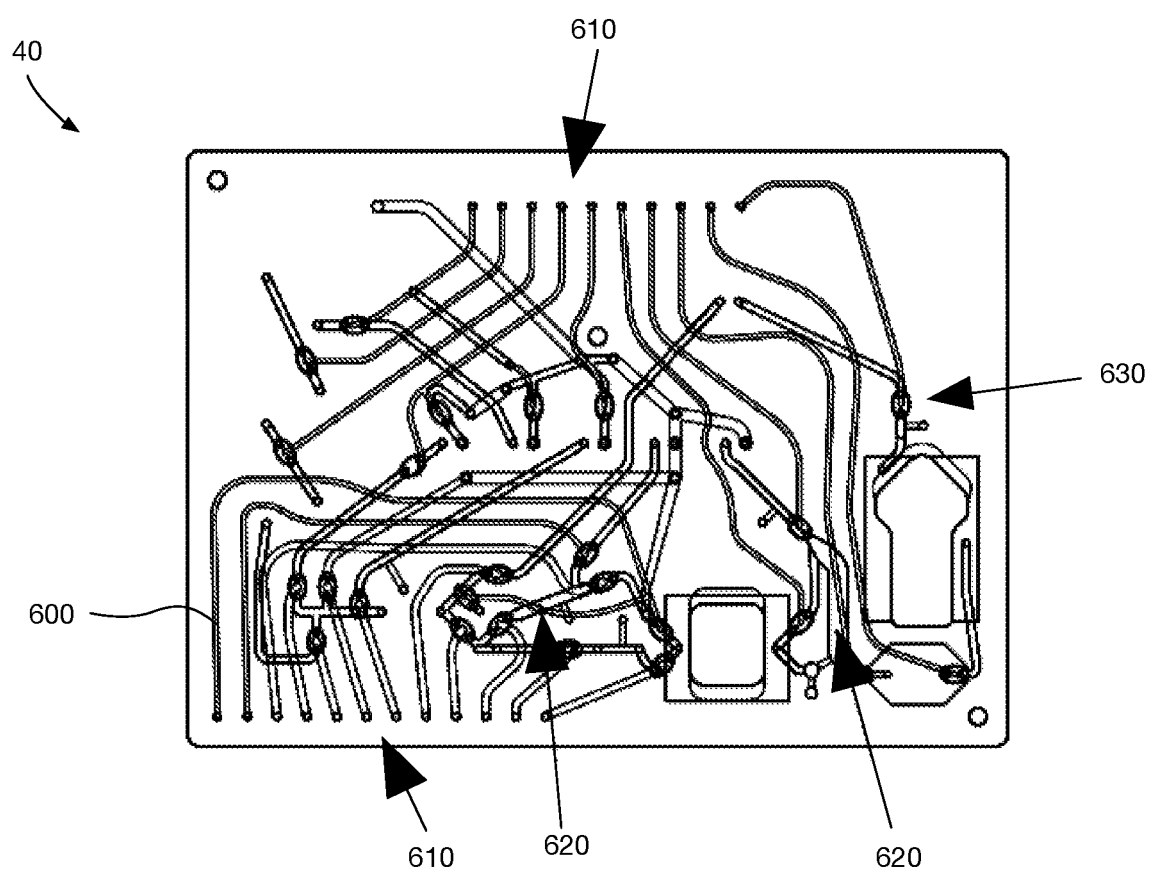
FIG. 6: A projection view of a iMFC card

FIG. 6 illustrates a composite "projection" image of all the layers of a iMFC card. In general, the card has one or multiple channels such as 600, such that fluids can flow from one location to another in these channels. The channels may be formed by cutting grooves into the material of a layer within the card. In addition, the card may also have one or multiple valves such as 630 and one or multiple channels or reservoirs such as 620 where volume may be metered. Some layers or section of the layers may be composed of the breathable membrane. The card may contain a number of ports such as 610. The ports may form an interface between the hardware and the card. These ports are used to apply drive pressure (to drive the fluids) or valve pressure (to control the valves). The location of these ports may remain the same for the cards, which prevents any need to modify the underlying hardware. However the card may be designed in any convenient manner and the functions on the card may be placed in any convenient manner. This aspect makes the card versatile as it may be designed for doing various tests without the need to change the underlying hardware.

Pneumatic System.

Figure 7:
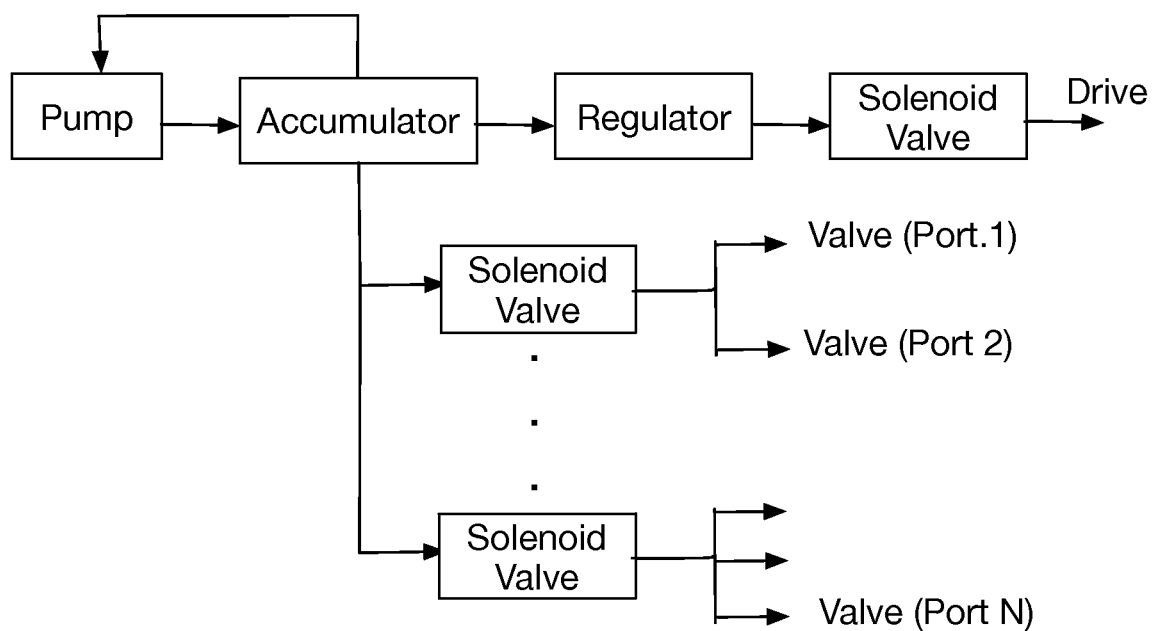
FIG. 7: A pneumatic system.

The pneumatic system (FIG. 7) is responsible for regulating the flow within the card. The pneumatic system may have a pump that may be located within the unit base. This pump compresses air in an accumulator to a desired pressure, such as 16 psi. The figure also indicates a feedback loop from the accumulator to the pump so that the pressure within the accumulator is kept constant. From the accumulator, one path leads to a regulator where the relatively high pressure of the accumulator is regulated down to a lower pressure, such as 6 psi. This lower pressure is used to drive the fluids within the entire system. A solenoid valve may be included at the output of the regulator, to turn on the fluid drive. Another path from the accumulator may go through one or multiple solenoid valves to control the opening or closing of the valves. Thus the relatively high pressure (16 psi) of the accumulator may be used to control the valves. As indicated in the figure, each solenoid valve may control one or multiple valves. FIGS. 5A and 5B depict how the flow of fluid is controlled through the design of the fluid channels and the air flow channels. In the context of FIG. 7, the fluid channels may be connected to the "Drive" output and the air flow channels may be connected to one of the "Valve" outputs.

The pneumatic system may be part of the hardware; hence some of the pathways for supplying the pressure for the fluid flow or for valve control may not be modified easily. However to achieve flexibility of design of the card, only the ports are required to be at the same location; these ports are how pressure is supplied to the air flow channels to control the valve or to the fluid drive channels. These ports are shown by 610 on FIG. 6. Thus by requiring the cards to have the ports at the same location, the same hardware unit may be used, but the cards themselves may be designed for different purposes.

Hardware.

Figure 8:
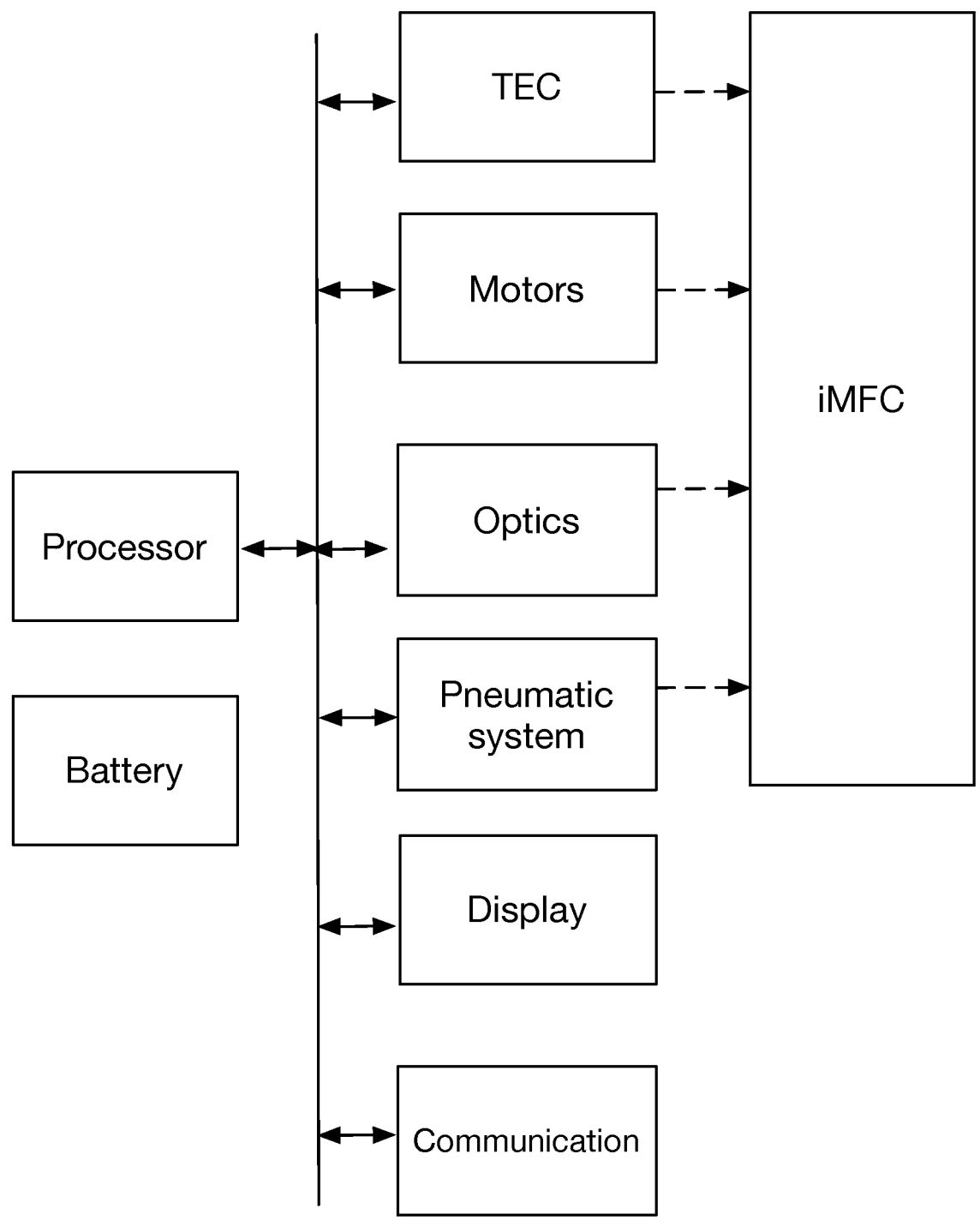
FIG. 8: A functional block diagram of the physical hardware of device 10.

As illustrated in FIG. 1, the testing system described may be built into a portable box, including a unit base 20 and a unit lid 30. Various functions and capabilities may be physically configured within the base and the lid. FIG. 8 illustrates a functional block diagram of the hardware. The hardware may include a processor and a power source such as a battery. The processor may interface with the other members such as the TECs, the motors, the optics system, the pneumatic system, the display and the communications system. With regards the display system, the device 10 may have a screen that may relay messages or the results. With regards the communication system, the unit 10 may be interfaced to an external computer via any suitable communication method such as ethernet and bluetooth. The display and communication subsystems these may be implemented using well-known techniques. FIG. 8 also illustrates that the card may be mechanically interfaced with some of the subsystems such as the TEC, the motors etc. These interfaces are illustrated by dashed lines.

Embodiments of our claimed invention include:

1. A molecular diagnostic device, system or method that detects a large set (>6, >10, >20 or >50) nucleic acid sequences without any human intervention to carry out the testing process, except for the purposes of injecting or inserting a sample and reading the results.

2. A device, system or method herein where the steps of lysis, purification, PCR and hybridization are integrated into one system and where these steps are carried out in a disposable card.

3. A device, system or method herein where the disposable card may contain modules so that by changing the modules, the card can be configured for different tests.

4. A device, system or method herein where the analytes may be detected in samples from a variety of sources including, for example: blood, saliva, GI samples, urine, wound swabs, spinal tap, nasal swabs, veterinary and agricultural sources.

5. A device, system or method herein where the tool used to collect the sample may be directly input into the card.

6. A device, system or method herein where the amplification step of the PCR process is done via a process called pan-amplification rather than sample splitting.

7. A device, system or method herein where the detection step uses a microarray.

8. A device, system or method herein where the microarray includes controls that verifies if each step of the testing process occurred appropriately.

9. A device, system or method herein where the detection step uses a real time hybridization method which predicts the concentration of the samples based on a kinetic model, wherein readout time is reduced.

10. A device, system or method herein where the PCR process is carried out in a passivated metallized chamber such that the temperature within the chamber can be controlled rapidly by locating the metallized chambers adjacent to and in contact with TECs, preferably where the metal used is aluminum.

11. A device, system or method herein where the volume of the solutions is metered through the use of channels or chambers coupled with a breathable membrane so that as the channel or the chamber fills up, air is forced out of the breathable membrane; hence the error from having air in a metered volume may be minimized or removed.

12. A device, system or method herein where a pneumatic system controls the fluid flow by applying different pressures to drive the fluids and to control the valves.

Detailed Description of Additional Embodiments and Examples Thereof

Disclosed is a portable system that can analyze nucleic acid sequence content in a variety of samples. The system is capable of taking in a variety of raw samples (diagnostic or environmental) and performing nucleic acid extraction, purification, amplification, labeling, and sequence analysis by microarray in a self-contained unit. The system is automated and rapid to allow for point of site analysis of samples by users who are not trained laboratory technicians.

In embodiments: the system comprises (1) a reusable hardware platform and (2) a consumable integrated microfluidics card (iMFC) that determines the assay to be performed;

the system is small (<150, <250, or 400 in3), light-weight (<3, 5 or 10 lb), fast, and intuitive to use;

the reusable hardware controls and provides the pneumatics, pressure regulation, temperature control, laser control, and imaging of the final microarray;

the iMFC consumable comprises a card that performs sample lysis, purification, PCR, and detection and houses all the required dry reagents; and/or the iMFC further comprises a reagent storage element that holds all the liquid reagents separately so as not to compromise the integrity of the dry reagents.

In embodiments the system provides:

Ease of Use: easy to operate and the results simple to interpret, for field use by untrained operators; configured to be Clinical Laboratory Improvement Amendments (CLIA)-waived; and/or provides sample-in to answer-out capability without user intervention.

Configurability: the iMFC is modular, enabling stocking of the main iMFC and attaching separate, quickly produced, lower-cost modules that define the end product assay functionality; since the main iMFC remains the same, the system provides just-in-time development of new assays as new threats emerge.

Assay Flexibility; flexibility in sample type (from hardy spores to easily ruptured mammalian cells) and/or analyte class (DNA, RNA, and protein).

Manufacturability and Cost; the iMFC and the modular components are manufacturable using low-cost injection molding or an advanced manufacturing laser converting process; high-speed laser converting and precision lamination allows manufacture of an iMFC with features as small as 125 μm and tolerances of less than 50 μm at production rates approaching 50 feet per minute; the combination of older injection molding technology and advanced laser converting technology allows production of complicated disposable cartridges for less than $10 per card at volume.

In embodiments our system is fully automated from raw sample input to answer out, and/or configurable to allow multiple analysis types.

In embodiments our system provides a portable bioanalysis platform to detect nucleic acids, typically DNA or RNA, such as microbial, typically bacterial, viral or fungal detection, and health monitoring via mRNA and protein detection, and cell selection and concentration. In an embodiment the system consists of two elements: (1) a reusable hardware platform and (2) a consumable integrated microfluidics card (iMFC) that determines the assay to be performed.

In embodiments our system is demonstrably adaptable to diverse applications:

Bacterial Agent Detection.

Our DNA detection iMFC operates in a manner similar to that of a laboratory work flow: lysis, DNA purification, DNA amplification and labeling, and hybridization. Our microfluidic technical approach to each step is highlighted below.

Lysis is accomplished using silica beads and low-cost disposable motors for robust lysis of sample types, from hardy spores to mammalian cells.

We purify DNA by binding the DNA to a silica frit, washing away impurities, and eluting in a polymerase chain reaction (PCR)-ready solution. Our DNA purification module and procedure allow elution of high DNA concentration in the first 6 μl in ~5 min with no user intervention. In contrast, a laboratory bench approach for spore lysis and DNA purification takes 30 min over 7 steps and requires laboratory centrifuges.

We perform DNA amplification in an aluminum-walled chamber between two custom thermoelectric coolers (TECs). The TECs and aluminum chambers allow for rapid heat transfer between the TECs and the PCR mix. We have demonstrated PCR duplex of the two genes (AGG and STX2) associated with the E. Coli O104:H4 pathogen in 12 min and have detected down to 10 genomic copies.

We hybridize DNA using a custom DNA microarray and optical system. Light is coupled into a glass slab using a grating and remains confined by total internal reflectance. The evanescent wave on the surface is used to excite the target sequences hybridized to their complement on the surface of the microarray. Use of the evanescent wave allows us to visualize hybridization in real time. A custom optical relay and CCD are used to image the surface of the microarray.

We can verify multiplex detection of multiple potential biological warfare agents and establish the receiver operator characteristic (ROC) curves for our assay and hardware platform.

Viral RNA Detection.

Our technical approach to detecting viral RNA is the same as our approach to DNA detection, except we use a single reverse-transcription/PCR mix. We have demonstrated a single master-mix reverse transcription and PCR in less than 30 min for the influenza H3N2 and H1N1 viruses. The field-portable capability can directly leverage the information obtained from DARPA's Prophecy program and allow early detection of potentially pandemic causing mutations in viral populations in domesticated animal herds or flocks.

mRNA Detection.

We can address mRNA analysis using the same hardware, updating the iMFC to allow for mRNA capture using poly-T beads and imaging of the microarray in real time to capture kinetic data. The use of kinetic measurements allows us to determine the concentration of each analyte well before equilibrium is reached, thereby reducing the hybridization time that typically drives gene expression analysis. Our capability to analyze a blood sample rapidly and at the point of need for mRNA leverages the investment DARPA made in the Predicting Health and Disease program.

Protein Detection.

We can transduce a protein-binding event into a nucleic acid readout, thereby giving our same platform the ability to assay for both nucleic acids and proteins. Plasma protein concentrations are indicative of health status or environmental exposure. We have developed a four-host-response protein panel indicative of ionizing radiation exposure; similar panels for other environmental exposure diagnostics can also be integrated into the platform. We used the same bead-capture microfluidic module as that for mRNA detection to capture protein analytes on a bead. The beads are functionalized with antibodies for particular protein analytes instead of poly-T oligonucleotides. A second antibody labeled with an oligonucleotide is used as the reporter molecule as in a traditional immunoassay. Once the sandwich assay has undergone a stringent wash, the reporter oligonucleotide is amplified, labeled, and hybridized using the same modules as for DNA detection. We call this approach "microsphere-immune-PCR" (MSiPCR).

Cell Selection and Concentration.

Our front-end module allows specific cell selection and concentration using a microfluidic electroactive (EAP) polymer cell sorter, analogous to laboratory-scale fluorescence-activated cell sorters (FACS). The module increases the operational envelope of the system by either concentrating a dilute cell concentration in a large volume (a few bacterial cells per ml) or sorting out select cells from a background of many cells (only activated T cells from all peripheral blood mononuclear cells). In this module we align cells using hydrodynamic and/or inertial focusing, and then sort based on a fluorescent trigger using EAP actuators. We have demonstrated the technology's potential to sort at speeds in excess of 25,000 cells/second.

Baseline Handheld Analyzer

The hardware platform provides all necessary hardware actuation required to support iMFC processing of a microbial DNA sample. The user interacts with the hardware platform via a computer USB port. Once the iMFC is inserted into the hardware and the lid is closed, the user selects a specific processing script for the desired assay. After the script is initiated, the handheld runs without user interaction, until completion. During the run, images are transferred from the handheld to the host PC, where they are analyzed. At the completion of the run, analysis and results will display on the screen for user review.

The hardware is designed to allow for cell lysis, purification, amplification and detection, in a small portable device, preferably with a total volume of less than 1 ft$^3$., preferably less than 200 in$^3$. In one embodiment the hardware dimensions are 4.75 in. deep×6.25 in. wide×5 in. high for a total volume of 148 in.$^3$.

On the iMFC, membrane valves and liquid fluid flow are controlled by positive pressure. The pneumatic subsystem is centered on a custom acrylic manifold that interconnects all pneumatic components in the handheld analyzer (HHA) and routes those component outputs to the input ports on the iMFC. This manifold contains an accumulator to hold a volume of air at a regulated pressure (18 psi) appropriate for microfluidic valve membrane actuation on the iMFC. A single solenoid is used to trigger drive pressure to the iMFC at any time during assay processing. This drive pressure port is routed through a pressure regulator (mounted to the integrated manifold), so that drive pressure can be adjusted between 0-10 psi for any given HHA.

Table 1 shows functional components and their purposes and implementation in the baseline system. The hardware that supports the amplification (PCR) and detection modules are described in detail below as part of the baseline iMFC description. The 2nd column lists the purpose of that functional component and the final column lists our technical approach implemented on the hardware platform for achieving the desired capability.

TABLE 1

| Functional Component | Purpose | Components |
| --- | --- | --- |
| Pneumatics | Solenoids control air flow to actuate membrane valves on iMFC to stop and start fluid flow, | Air accumulator, 22 pneumatic solenoids, pressure sensor, and integrated manifold to route air to iMFC pneumatic inputs. |
| Drive pressure regulator | Regulate drive pressure used to drive fluid flow on iMFC. | Pressure regulator, 1 pneumatic solenoid. |

TABLE 1-continued

| Functional Component | Purpose | Components |
| --- | --- | --- |
| Amplification (PCR) | Rapid thermocycling of small volume reaction. Support for near continuous thermocycling. | Two thermoelectric coolers (TEC) and heat sinks. |
| Hybridization station | Temperature-controlled stringency to improve hybridization specificity. | One TEC and heat sink. |
| Detection station | Normal incidence 635 nm laser illumination of optical grating on iMFC microarray. 647 nm filtering and CCD image capture of hybridized sample label fluorescence. | 10-mW, 635 nm laser diode, focusing optics, line-generating optics, turning mirror, 647 nm interference filters, relay lens, CCD chip, and supporting electronics. |
| Lid Enclosure | Small form factor enclosure to hold iMFC with sufficient force to ensure pneumatic sealing. | Hinging lid mechanism and translating lid to allow for iMFC thickness variability. |
| Electronics and power | Power and electrical signaling required by all powered components. | Circuit boards, wiring, Li-ion battery. |
| External I/O | Power plug input port and laptop communication port. | AC power supply input, USB Type-B, battery connection. |

Baseline iMFC and iMFC Modules

The iMFC consumable comprises (1) a card that performs sample lysis, purification, PCR, and detection and houses all the required dry reagents and (2) a reagent storage element that holds all the liquid reagents separately so as not to compromise the integrity of the dry reagents. Because the iMFC was designed in a modular fashion—i.e., application-specific modules are assembled onto a generic card—the iMFC for new applications can be easily and quickly developed by simply interchanging the modules. This versatility feature eliminates the need to redesign, develop, and manufacture new cards, the most complex component. Once fabricated, the same cards can be used for a wide range of applications, thereby reducing cost and development time.

Microfluidic Card.

The card utilizes positive-pressure-driven flow and consists of three functional layers that contain (1) fluid channels, (2) 22 membrane valves to control fluid flow, and (3) vents for bubble removal from the fluid channels. These functional layers together are composed of nine laminate layers surrounded by two injection-molded parts. Seven modules are pre-mounted on the card, four on the top surface (lysis module, purification filter, PCR master mix chamber, and primers chamber) and three on the bottom surface (PCR chamber, stir bar mixer chamber, and detection chamber). Affixed to the detection chamber is the optical waveguide chip, which contains a DNA microarray to sense the targets of interest.

Reagent Block.

When the user starts the program, an inflatable bladder in the handheld hardware presses the reagent block onto the sharps to pierce the foil seals, which, in turn, releases the liquid reagents. With positive-pressure-driven flow, air enters each chamber in the reagent block and drives the liquid reagents through the outlet vias and into the card. Compressible gaskets on the card prevent fluid or air leakage at the reagent block-card interface. Table 2 identifies liquids that can be stored in the reagent block for DNA analysis. Cards designed for different application (mRNA or protein analysis) will have different reagents. The reagent block also includes a waste reservoir that contains absorbent material to collect the reagents that flow through the card. The reagent block preferably contains all the liquid reagents in a single prepackaged format required for biological assay analysis. The table lists the reagents currently used for DNA analysis. The buffer name is specified along with the purpose of the buffer and the exact chemical formulation. The reagent block is general purpose, and the required reagents will change depending on the biological assay being performed by the iMFC. Our technical approach is to use the same package but fill it with different reagents to support the new assay capabilities for RNA virus detection, mRNA detection, and protein detection.

TABLE 2

| Reagent | Purpose | Contents |
| --- | --- | --- |
| Lysis buffer | Prepare sample for lysis | Bead-beating solution from MO BIO PowerSoil DNA Isolation kit modified with 1% phenol (w/v) to add a denaturant and 1% n-octanol (w/v) to prevent foaming |
| Wash buffer | Wash sample during purification | 80% (v/v) Ethanol |
| Elution buffer | Remove and collect purified sample from purification filter | 10 mM Tris buffer, pH 9.2 |
| Water | Dilute residual PCR inhibitors in purified sample (if necessary) | Deionized water |
| Hybridization buffer | Prepare amplicons for hybridization on the microarray | Saline-sodium phosphate EDTA (SSPE) buffer 20x concentrate |

Lysis.

Following the release of liquids from the reagent block, the next step in the automated program is lysis. The lysis module, which can handle even spore samples, consists of three chambers: the sample chamber, the bead beating chamber (for spore lysis), and the binding agent chamber. After lysis buffer from the reagent block flows into the sample chamber, a motor turns on to mix the lysis buffer with the sample. The mixed sample then flows into the bead-beating chamber, where a second motor runs for 3 min to agitate glass beads and lyse the spore sample via bead beating. The lysed sample then enters the binding agent chamber, where a solid mixture of guanidinium hydrochloride and sodium bisulfate (the binding agent) dissolves in the sample to facilitate binding of DNA to the purification filter in the next step.

As a proof of concept for this approach, we obtained lysis efficiency data from samples of B. subtilis spores lysed by the lysis module. Spores represent the most challenging lysis situation. For non-spore applications, the bead-beating chamber can be exchanged with a motorless chamber module to simplify the design and reduce costs.

Purification.

We faced several challenges in developing a technical approach for microfluidic DNA purification. For example, we needed to develop an approach that replicated a laboratory procedure requiring 7 steps and 30 min with multiple centrifugation steps to successfully lyse and purify a spore sample. Additionally, we needed to elute the DNA in the first 6 μL fraction. In a laboratory assay the purified DNA is typically eluted in a larger volume (e.g., 20 μL), and then a smaller volume aliquot (1-3 μL) is used for PCR amplification. In this situation the DNA is mixed and therefore elution rate is averaged over the entire 20 μL. A microfluidic approach involves little mixing since most of the flow is laminar; therefore, the highest concentration of eluted DNA needs to be in the first fraction.

TABLE 3

We performed three replicates of B. subtilis spore lysis using our lysis module. The results are shown below in percentages from the starting stock of 10⁷spores (based on a viability count). The control was a Claremount bead-beating device. Our microfluidic results are comparable to the control using laboratory pipettes and tubes.

| B.subtilis Sample Number | Recovery after Lysis (%) Based on Viable Count Input of $10^7$ |
|---|---|
| 1 | 48.4 |
| 2 | 31.6 |
| 3 | 18.6 |
| Average | 32.9 |
| Control | 39.6 |

On the iMFC after lysis, the sample flows through the purification module, DNA binds to the filter, and the contents of the remaining lysed sample flow to the waste reservoir. Wash buffer from the reagent block then flows through the filter to remove residual impurities and also collects in the waste reservoir. Air blows through the purification module to dry the filter, followed by elution buffer (a key aspect to achieve significant elution in the first fraction is the elution buffer pH) from the reagent block, which, as it flows through, removes the purified DNA from the filter in preparation for PCR. Table 4 presents the data for three replicates of E. coli samples purified on the microfluidic card and compares the results with those from a standard purification filter. In each case it is clear the highest concentration is coming out in the first fraction. Each fraction represents ~6 μl of DNA in elution buffer.

TABLE 4

We repeated three replicates of E. Coli sample purification using our iMFC protocol. We developed the protocol to elute most of the DNA in the first fraction, since we will not have an opportunity to pool the entire elution and select just a fraction with a pipette as with typical laboratory bench approaches. The results clearly indicate the largest concentration comes in the first 6-μl fraction.

| | Sample 1 | Sample 2 | Sample 3 |
|---|---|---|---|
| Fraction 1 in ng/μl | 7.5 | 1.5 | 0.7 |
| Fraction 2 in ng/μl | 5.5 | 1.3 | 0.4 |
| Fraction 3 in ng/μl | 3.2 | 1.1 | 0.4 |
| Laboratory bench control in ng/μl | 11.0 | 3.3 | 2.6 |
| Percent compared to laboratory | 67.8% | 44.0% | 27.8% |

PCR Amplification and Labeling.

Carrying the purified DNA from the filter, the elution buffer fills the PCR master mix chamber, which contains lyophilized master mix. Then the rehydrated master mix flows into the primers chamber and rehydrates the dried primers. We have separated the primers and master mix to allow for reuse of generic PCR master mix modules. The lyophylization of oligonucleotides is quick, and this approach allows us to support rapid deployment of kits to test for emerging threats. Following the rehydration steps, the sample—along with the master mix and primers—enters the PCR chamber, where the sample DNA is then amplified.

Two key features enable us to accomplish rapid PCR: (1) aluminum PCR module surfaces and (2) a novel TEC assembly that can ramp >15° C./s with accuracy of ±1° C.

The PCR module is sandwiched between two TEC assemblies. The PCR master mix is held in a 1-mm-tall acrylic chamber enclosed by two 25-μm aluminum walls. The aluminum surfaces of the PCR chamber enable fast conductance of heat to and from the TEC assembly to the liquid PCR mix. As a comparison, a 50-μm-thick plastic slows the ramp rate down by ~3×.

SRI designed and tested a custom TEC assembly. We have transitioned the design to RMTltd for fabrication. The custom SRI assembly combines a heat sink, a TEC, a feedback sensor (thermistor), and an aluminum nitride (AlN) thermal spreader that surrounds the sensor. Each thermistor sensor is calibrated to allow the HHA to compensate for any sensor manufacturing error tolerance.

As a proof of concept for our PCR system, we created a duplex PCR assay for the aggregative adherence fimbriae (AGG) and Shiga toxin (STX2) genes associated with the E. coli O104:H4 pathogen from the 2011 German outbreak. The primer and probes were selected for unique regions based on sequence analysis uploaded by BGI shortly after the outbreak began. A laboratory assay using benchtop equipment was used to establish probe selection and primer optimization for AGG and STX2 targets. Once established, the assay was transitioned to the SRI microfluidic PCR system. Since the SRI PCR system takes advantage of the aluminum PCR chambers optimized for heat conduction and temperature uniformity and the novel thermistor-driven TEC design for rapid temperature cycling, a custom master-mix formulation with adjuvants used to passivate aluminum chambers allowed for duplex amplification of AGG and STX2 targets in 16 min.

Results provided an overlay of 40 PCR cycles (95° C. denature step, 62° C. anneal and 73° C. extension). Each cycle lasts 21 s for 40 cycles, totaling 14 min of PCR thermocycling. The remaining time is for initial denature and uracil-DNA glycosylase (UNG) treatment. Our custom master mix contains dUTPs as part of the amplification, and the UNG step ensures there is no contamination between different uses of the hardware platform. We tested the 16-mM PCR at five different input copy numbers (10, 50, 100, 500, and 1,000) and quantified the amplification factor for both the AGG and STX2 genes. Additionally we tested a 500 copy input using a 12-min PCR protocol and observed that the cycle time was reduced from 21 s per cycle to 15 s. Again, 2 mm of UNG treatment and initial denature were used, for a cycling time of only 10 min. Table 5 shows the results of nested PCR against amplicon standards to quantify the amplicons in each sample and determine amplification factors. Overall we had an amplification range of $1.6 \times 10^9$ to $3.4 \times 10^{11}$ for modular PCR. In addition, amplicons generated with modular PCR systems have been detected with the SRI modular hybridization system.

TABLE 5

Quantitation results of modular PCR samples. Results indicate all samples would have >3.4 nM of amplicon in the hybridization, which is above the 1-nM LOD.

| PCR Input (copies) | PCR Total Time (min) | AGG Amplicon Conc (ng/µl) | AGG Molarity (nM) | AGG Amp Factor | STX2 Amplicon Conc (ng/µl) | STX2 Molarity (nM) | STX2 Amp Factor |
|---|---|---|---|---|---|---|---|
| 500 | 12 | 5.2 | 55.8 | 2.33E+09 | 3.7 | 39.59 | 1.65E+09 |
| 10 | 16 | 0.1 | 1.0 | 2.08E+09 | 0.6 | 6.68 | 1.40E+10 |
| 50 | 16 | 76.5 | 816.2 | 3.41E+11 | 11.0 | 116.93 | 4.89E+10 |
| 100 | 16 | 110.6 | 1180.0 | 2.47E+11 | 26.6 | 284.01 | 5.93E+10 |
| 500 | 16 | 43.6 | 464.9 | 1.94E+10 | 11.5 | 122.62 | 5.12E+09 |
| 1000 | 16 | 129.6 | 1382.9 | 2.89E+10 | 34.3 | 365.57 | 7.64E+09 |

Detection.

To detect the presence of specific targets, the amplified sample is hybridized to the microarray on the optical waveguide chip. To facilitate hybridization, SSPE buffer from the reagent block is first added to the amplified sample. Two metering chambers are utilized to achieve the optimal ratio of sample to SSPE buffer.

The SSPE and PCR product are mixed and then pushed into the detection chamber, which incubates the sample over the microarray on the optical waveguide chip. After 5 min of temperature-controlled hybridization using our custom TEC assembly, additional SSPE buffer flows into the detection chamber to wash out the sample and remove unhybridized amplicons, followed by a rise in temperature to remove cross-hybridization or any amplicons that are nonspecifically bound to the wrong probes.

Finally, the DNA microarray is imaged using a custom illumination, collection, and imaging optical block. The optics block is designed as a standalone subcomponent that includes everything necessary to laser illuminate and image the microarray hybridization. The optics block can be pre-aligned and adjusted before installation into the HHA. Once this pre-alignment is performed, there is no need for further adjustment at the time of installation.

The laser illumination optics consists of a line-generating laser diode module and a turning mirror. The target for the laser illumination is the grating on the microarray chip. The line-generating laser diode emits a 10-mW beam at 635 nm in a rectangular pattern to excite the Alexa Fluor 647 nm dye molecules used to visualize hybridization to the microarray. The line-generating diode module has focusing and line-generating optics integrated into an off-the-shelf package (Coherent).

The microarray imaging optics comprises a folded 1:1 relay lens and interference filters. The custom-designed relay lens group is fast (at f/1.5) for maximum light-gathering capacity. It is small in size (12 mm in diameter and <27 mm long). The relay lens is designed to sufficiently collimate light into the two interference filters (made of dielectric stacks) used to reject laser excitation light and scattered light from reaching our monochrome CCD imager.

The CCD chip and electronics are connected directly to the microarray imaging optics to reduce noise and minimize signal loss. The CCD is capable of sufficient readout speeds for microarray analysis (4 frames/s), and sufficient signal-to-noise for microarray imaging without the need for CCD cooling.

As a proof of concept for the optical system, we hybridized the PCR amplicons generated by the SRI aluminum PCR chambers and the TEC assemblies and read out the results using the described optical system. The test protocol included spotted probes (as identified by our rapid DNA synthesis instrument), on-board incubation at 37° C. for 5 min, multiple stringency washes at increasing temperatures from 37° C. to 60° C., and the optics package for automated image capture. We hybridized a negative control with only control (A3) analyte, the resulting amplicon from 10 copies into PCR, and the amplicon from 50 copies into PCR. Assay results have proven selectivity by hybridizing negative control samples and samples amplified from individual primers for AGG and STX2. The images of the hybridization demonstrated that the target probes are clearly visible in both the 10- and 50-input template cases and not present in the A3 control case.

Low-Cost High-Volume Manufacturing of the iMFC Consumable.

We developed a manufacturing process plan to drive down the costs of iMFC fabrication for high-volume production. Because injection molding is a simple, inexpensive method to create parts, we injection-mold both the top and bottom layers of the card, as well as the lysis module and reagent block. The remaining laminate layers of the card are fabricated in an automated roll-to-roll process, in which rolls of materials are laminated together, laser cut, and then rewound into another roll, all on the same equipment system in a rapid pipelined fashion. With high production volumes on the order of millions of cards, the cost may become as low as $10 per card.

DNA Detection Approach.

Our system has the capability to photolithographically synthesize oligonucleotide arrays with all possible probes to an amplicon in less than 10 hours, so we can select appropriate probes and transition a bench PCR assay to our platform in about 2 weeks. As shown herein, we have successfully demonstrated this capability to develop an amplification assay, transition it to iMFC PCR, and select probes for the *E. Coli* O104:H4.

Viral RNA Detection Approach.

RNA virus detection uses all the same modules as for DNA detection, with a microfluidic assay for reverse-transcription of an RNA virus genome and amplification. We have demonstrated proof of concept of this approach using an assay that can distinguish seasonal and swine influenza. The approach taken to develop the influenza assay is generalizable, and can use the same approach for select agent RNA viruses.

For identification of influenza, our first step was to identify primers that would selectively amplify a segment of the influenza A matrix gene as well as portions of the hemagglutinin gene that distinguish H1(swine) and H3(seasonal) strains. Our RT-PCR protocol involves a 5-min reverse-transcription (RT) step at 42° C., where the reverse primers anneal to the RNA target and initiate synthesis of the first DNA strand. A 2-mM reverse-transcriptase deactivation and simultaneous Taq polymerase "hot start" then allows the forward primers to anneal to the first DNA strand and synthesize the second DNA strand. At this point, 40 cycles of PCR commence with 10-s denature at 95° C., 20-s anneal at 62° C., and a 5-s extension at 75° C. Once good amplification is achieved in a benchtop instrument we move to our modular amplification system, which simulates amplification in our iMFC. Because of fast temperature ramping in this system, the RT-PCR protocol described above takes <33 min. RT-PCR products are evaluated first using gel electrophoresis and then on a microarray. Gel electrophoresis results for modular amplification of matrix and hemagglutinin genes for CA 2009 swine flu strain (H1N1) and HK 68 seasonal strain H3N2 (a triplex amplification) were obtained. The 244 bp amplicon indicates the influenza A matrix gene. The hemagglutinin amplicon for the H1 strain is 173 base pairs, while the H3 amplicon is 177 base pairs. Hybridization to sequence specific probes on a DNA microarray gives unambiguous differentiation of the H1 and H3 strains.

The first step in achieving sensitive and selective detection on a microarray is preparation of a photolithographically synthesized probe selection chip containing 20-25 mer probes that cover the entire amplicon for our targets of interest. Our ability to synthesize in less than a day all possible probes to an amplicon of interest means we can empirically test for sensitive and specific probes. Next we performed hybridization experiments to the microarray to select the most sensitive and specific probes. A selection of probes that readily distinguish the H1 and H3 were identified; there are a few regions of the amplicon that easily differentiate between the two amplicons. The best probes can be fitted with an amine modification for spotting on epoxy functionalized microscope slides or waveguide chips to be used in our handheld device.

mRNA Detection Approach.

Gene expression profiling of peripheral mononuclear cells (PBMCs) is a useful method of monitoring disease status, environmental exposure, and pre-symptomatic diagnosis of infection. Our iMFC capable of mRNA expression analysis uses a slightly modified version of the hardware platform—an extra TEC and increasing illumination uniformity on the microarray, and can perform:

PBMC selection and lysis: using commercial size exclusion filters for PBMC purification from whole blood, and the cell selector module described herein.

mRNA purification: capture the mRNA from lysed cells using microspheres coated with poly-T oligonucleotides.

T7 linear amplification and labeling: use the current PCR chamber for T7 amplification and labeling and commercially available kits.

Rapid Hybridization: use kinetic measurements of hybridization to determine analyte concentration; reduce the time required for gene expression hybridizations from many hours to minutes.

T7 amplification leverages existing iMFC PCR modules and commercially available kits.

mRNA Purification.

For mRNA purification we use a microfluidic purification module that can hybridize mRNA to polyT coated beads, wash away containments, and then release the mRNA from the polyT beads. We use a mixer that keeps ~5 μm microsphere beads in solution and a new TEC to melt the captured mRNA from the beads after a wash step. We have tested the device to verify that 5-μm beads move well between the bellow mixing chamber and the filter. We have also demonstrated that the fluid can be heated to ~80° C. to allow for denaturing of the polyT:mRNA duplex.

Rapid Hybridization.

To decrease hybridization time and improve repeatability we infer concentration from the kinetic rate parameter. In situations where the number of target transcripts is in excess compared to the number of probes, the signal value vs. time should follow a kinetic curve:

$$Y=C(1-e^{-rt}), r=k_{off}+[A]k_{on}$$

In the equation, Y is the background-subtracted signal; $k_{off}$ and $k_{on}$ are kinetic parameters dependent on temperature, gene sequence, and probe shift; [A] is the concentration of target gene in solution; and C is a scale factor depending on multiple factors including light intensity, probe density, target concentration, and kinetic parameters. Our probe selection technique estimates koff and kon by fitting the equation to the time series of hybridization signals across multiple concentrations. These estimates can be stored and used in real time to estimate [A]. Because variations in light intensity and probe synthesis density affect the parameter C but not the variables inside the exponential, this kinetic technique significantly improves chip-to-chip and same-chip replicate repeatability.

As a proof of concept, we have experimented with the kinetic rate approach, starting with synthesized 25-base-pair oligomer targets. In one probe's kinetic response to the A3 control labeled oligonucleotide. Each line represents the response to a different concentration of A3: 50 nM, 100 nM, 300 nM. A nonlinear least-squares fit is used to estimate the parameters C and r for each time series. Then, experiments at multiple concentrations [A] reveal the affine relationship between r and [A].

We identify conditions that create a sensitive, repeatable relationship between r and [A]. Our data show that the relationship can occur in the right direction, with r=(0.0031, 0.0033, and 0.0058) s−1 for [A]=(50, 100, 300) nM. An additional benefit of kinetic curve fitting is that even if the equilibrium value C proves to be better than the kinetic rate r, the fitting process averages out short-term noise. We also note that the ability to measure kinetic parameters depends on the iMFC's use of an evanescent wave to excite only fluorescent molecules that are bound to the chip surface, giving a high signal-to-background ratio even while the target solution is in place.

Protein Detection Approach.

One way to expand the detection capabilities of the iMFC platform to include protein biomarkers is the microsphere immunoassay, which uses antibodies labeled with an oligonucleotide to create a nonlinear amplifiable DNA target when the target antigen is present, and we have developed an immunoassay module with the iMFC platform based on SRI's demonstrated microsphere immune-PCR assay (MSiPCR). Biotinylated target-specific antibodies are conjugated onto streptavidin-coated 6-μm polystyrene beads for initial capture of target antigen. Separate target-specific antibodies are chemically conjugated with one oligonucleotide for a second capture event of the target protein. Extensive washing between the two protein capturing events wash away any unbound target as well as free conjugates. The remaining bead portion is then amplified using a specific labeled primer set along with a taqman probe. The amplified nucleic acid signal is subsequently hybridized onto a microarray for detection and readout. We have migrated our benchtop assay to the iMFC platform: our proof-of-concept modular system for the iMFC platform incorporates a bellows mixer for washing and incubation steps, along with a filter to catch the beads after nucleic acid amplification System Improvements.

The optics block can be modified to provide a more uniform pattern into the microarray grating, and to use 532 nm excitation to improve detection signal-to-noise ratio. The process to switch from a 635 nm to 532 nm excitation light source is only a matter of changing the grating pitch.

This modified optics block consists of both laser target illumination optics and microarray imaging optics. The laser target illumination optics uses a small diode-pumped solid-state (DPSS) laser module, scanning and focusing optics, and a 2D scanning microelectromechanical systems (MEMS) mirror. The DPSS laser module can output a 40-mW laser beam at 532 nm for exciting Cy3 dye molecules. The beam can be focused on the MEMS mirror using the focusing optic. The 2D MEMS mirror can scan the spot over a rectangle and aim the beam at the grating. After reflecting off the scanning mirror, the beam hits the scan lens, which collimates the beam before it enters the grating on the microarray chip.

This system scans the same laser spot over the entire grating, and thus over the entire microarray. This eliminates illumination nonuniformity from the line-generating optics which can vary as much as 25% in intensity. The scan lens also allows us to collimate the beam before it enters the microarray chip grating. We validated with a proof-of-concept demonstration of the new scanning technical approach. The microarray imaging optics are unchanged from the current optics block, with the exception of filters for the different excitation (532 nm) and emission (570 nm) wavelengths.

REFERENCES

1. Niemz, A., T. M. Ferguson, and D. S. Boyle, Point-of-care nucleic acid testing for infectious diseases. Trends Biotechnol, 2011. 29(5): p. 240-50.
2. Bissonnette, L. and M. G. Bergeron, Infectious Disease Management through Point-of-Care Personalized Medicine Molecular Diagnostic Technologies. Journal of Personalized Medicine, 2012. 2(4): p. 50-70.
3. Foudeh, A. M., et al., Microfluidic designs and techniques using lab-on-a-chip devices for pathogen detection for point-of-care diagnostics. Lab Chip, 2012. 12(18): p. 3249-66.
4. Easley, C. J., et al., A fully integrated microfluidic genetic analysis system with sample-in-answer-out capability. Proc Natl Acad Sci USA, 2006. 103(51): p. 19272-7.
5. Xu, G., et al., A self-contained all-in-one cartridge for sample preparation and real-time PCR in rapid influenza diagnosis. Lab Chip, 2010. 10(22): p. 3103-3111.
6. Ferguson, B. S., et al., Genetic analysis of H1N1 influenza virus from throat swab samples in a microfluidic system for point-of-care diagnostics. J Am Chem Soc, 2011. 133(23): p. 9129-35.
7. Lam, B., et al., Polymerase chain reaction-free, sample-to-answer bacterial detection in 30 minutes with integrated cell lysis. Anal Chem, 2012. 84(1): p. 21-5.
8. Chen, D., et al., An integrated, self-contained microfluidic cassette for isolation, amplification, and detection of nucleic acids. Biomed Microdevices, 2010. 12(4): p. 705-19.
9. Chen, Z., et al., Development of a generic microfluidic device for simultaneous detection of antibodies and nucleic acids in oral fluids. Biomed Res Int, 2013. 2013: p. 543294.
10. Schumacher, S., et al., Highly-integrated lab-on-chip system for point-of-care multiparameter analysis. Lab Chip, 2012. 12(3): p. 464-73.

Embodiments of our claimed invention include:

1. An automated nucleic acid analysis system comprising in microfluidic connection sample lysis, purification, PCR and detection modules configured to detect in parallel distinct nucleic acid sequences via multiple sequence amplification and simultaneous microarray hybridization readout.

2. The system of a foregoing or subsequent claim wherein: the detection module comprises microarray detection optics comprising a microarray scanner employing evanescent wave excitation and detection; the detection module comprise an automated hybridization processor configured to provide multiple stringencies via temperature; and/or the PCR module is configured to perform reverse transcription and PCR in a single reaction.

3. The system of a foregoing or subsequent claim comprising an integrated microfluidics card comprising the modules and an analyzer comprising a receptacle configured to receive the card, operators configured to operate the card, and a controller configured to electronically control the operators, the operators comprising fluidic actuators, PCR thermal cycler, and automated hybridization processor and microarray detection optics.

4. The system of a foregoing or subsequent claim further comprising a reagent module configured to contain and deliver reagents to the lysis, purification, PCR and detection modules.

5. The system of a foregoing or subsequent claim that is:
    portable: less than 2000, 1000 or 500 in$^3$ and less than 50, 25 or 10 lbs;
    rapid: analysis in less than 60, 120, 180 or 240 minutes;
    multiplex: simultaneous analysis of more than 10, 50, 500 target sequences; and/or
    automated: requiring no user intervention between sample introduction and result display.

6. The system of a foregoing or subsequent claim wherein:
    the sample comprises protein analytes and the system is further configured to tag the protein analytes with tags comprising the nucleic acid sequences;
    anchored probes define the sequences by their spatial locations;
    the amplification is effected/achieved by a number of primers pairs less than the number of sequences being analyzed;
    the distinct nucleic acid sequences are of multiple species/organisms;

the PCR module comprises a metallic (e.g. aluminum) PCR reaction chamber;

the microfluidic connection comprises a breathable membrane configured for bubble removal, wherein the breathable membrane is underneath the channel layer, so the entire channel can be exposed to atmospheric pressure (in a particular embodiment, this membrane spans the card because it is easier to manufacture it as a layer than individual pieces, though it is only functional under the channel layers);

amplification is fully contained in the consumable (no open tubes, etc.); and/or detection is based on probe sets rather than primer sets (easier to build new tests).

7. The system of a foregoing or subsequent claim configured to:

amplify in a single vessel (no sample splitting);

receive and process analyte samples of blood, saliva, GI samples, urine, wound swabs, spinal tap, nasal swabs, veterinary and agricultural sources;

receive samples via a specimen collection tool or transport media;

process sample volumes between 1-100 ul;

be modular (modules can be interchanged to support different applications);

be capable of metering (done by channel dimensions and bubble removal); and/or be one directional and self-sealing (prevents sample cross contamination).

8. The system of a foregoing or subsequent claim comprising an integrated microfluidics card comprising the modules and an analyzer comprising a housing (box) and within the housing receptacle configured to receive the card, wherein the analyzer:

engages the card to perform the lysis, purification, PCT (amplification and labeling), and detection;

interacts with the sample via pressure (e.g. sample transport), magnetic fields (e.g. sample mixing), temperature (e.g. amplification, stringency, hybridization) and/or light (e.g. hybridization detection); and/or performs the detection by coupling an evanescent wave with the sample to observe hybridizations in real time and/or determining kinetics and possible base-pair mismatch which result in sequence information.

9. The system of a foregoing or subsequent claim comprising an integrated microfluidics card (cartridge) comprising the modules, wherein the card is configured:

to be specific to disease type (ex. respiratory illnesses);

to be specific to patient type (ex. pediatric);

to be specific to pathogen type (ex. biowarfare agents);

to be specific to individual (ex. pharmacogenomics);

to contain unique identifiers for paient-specific information;

for one-time use to maintain sterility and minimize cross-contamination;

to be produced using roll-to-roll manufacturing steps; and/or from a polycarbonate chassis, metallic foil PCR chambers, acrylic components, breathable membrane materials, and/or polyurethane seals.

10. The system of a foregoing claim functionally integrated with a microfluidic fluorescence-activated cell sorter (µFACS) configured to provide hydrodynamic and/or inertial focusing for particle or cell alignment and comprising microscale electroactive polymer (EAP) actuators configured for sorting.

11. A method comprising using the system of a foregoing claim to detect in parallel distinct analyte nucleic acid sequences via multiple sequence amplification and simultaneous microarray hybridization readout.

Detailed Description of Additional Embodiments and Examples Thereof: High-Performance Fluorescence-Activated Sorting (FACS) for Novel Point-of-Care, Portable, and Highly-Integrated Applications High-end commercial FACS instruments achieve sort rates of 10,000 to 40,000 sorts/s by electrostatically deflecting cells contained within charged droplets. [1, 2] They can be applied to a wide range of applications, for example, isolation of cancer-targeting T cells for immunotherapy, enrichment of stem cells for tissue engineering, and separation of specific cells for manipulation or further analysis (e.g., DNA sequencing, RNA expression, and fluorescence in-situ hybridization). However, they are large, expensive instruments that require expert operators, and thus are not suitable for point-of-care or portable applications. Additionally, their monolithic nature means they cannot be easily integrated with other instruments or processes.

In an attempt to address these limitations, researchers have developed many varieties of microfluidic FACS. Until recently, these devices were slow (more than an order of magnitude slower than conventional FACS), and most were difficult to fabricate or otherwise inappropriate for manufacturing and practical application. With the development of pulsed laser-activated cell sorting (PLACS), the microfluidic state of the art increased to ~10,000 cells/s with high purity [3]. In PLACS, cells are sorted using a fluid jet produced by a rapidly expanding and contracting plasma bubble. While the fluidic device is simple, inexpensive, and disposable, the system requires a high-repetition-rate pulsed laser, which is both expensive and large. Thus, PLACS fails to address the challenges of scale and expense.

We disclose a simpler approach to fluid actuation based on EAPs, which are polymers that change shape in response to electrical stimulation. They have been used in microfluidic devices to change the cross-sectional geometry of channels, generating small injections for electrophoretic separations [4], modifying the fluidic resistance of a channel and clearing blockages [5]. We have developed a novel, high-performance microfluidic EAP (µEAP) actuator and integrated it into a micro-FACS.

Electroactive Polymer Actuation.

Our fluidic actuator comprises a dead-end fluid chamber in which one or more surfaces comprise an EAP. In one implementation the floor of the chamber is an electrode covered with a thin (~12 µm) EAP layer of dielectric elastomer (silicone). Conceptually, the silicone acts like a flexible capacitor. It distorts when a voltage is applied to the electrode, increasing the chamber volume and drawing fluid into the chamber. When the voltage is released, the silicone relaxes and pushes fluid from the chamber.

EAP actuators are easily fabricated using proven microscale manufacturing techniques. To create actuators, we pattern electrodes onto an indium-tin-oxide-coated slide, which becomes the base substrate. We then spin a layer of uncured silicone onto the slide and thermally cure it. To create the channel layer, we mold microfluidic channels using conventional soft lithography. We then complete the devices by aligning and plasma-bonding the channel layer to the silicone-coated slide. The actuators' compatibility with soft lithography means they can be readily integrated into a large existing library of microfluidic devices. It also enables rapid prototyping. The devices are inexpensive because they require only a voltage source for actuation, and the fabrication approach is amenable to low-cost manufacturing.

In particular exemplification we fabricated actuators <1 mm$^2$ that demonstrate response times of 10 μs; however, the actuator size can also be micron scale (e.g. less than 1, 10 or 100 μm$^2$) and response times can be less than 10, 1, 0.1 μs. that shorter response times. Their size options makes them particularly amenable to both handheld and integrated applications and for parallel operation to increase.

The rapid response rate of these exemplifed EAP actuators (<20 μs) also indicates that they sorting rates of >25,000 cells/s. The devices are inexpensive because they require only a voltage source for actuation and are built using low-cost micro-fabrication techniques. The use of silicone as the polymer enables the simple integration of EAP actuators with microfluidic channels via soft lithography. This allows both rapid prototyping and the potential for scale-up to manufacturing quantities. EAP μFACS delivers throughput equivalent to benchtop FACS in a handheld format.

We have optimized the performance of the EAP μFACS and incorporated the improved device into a cell-concentration/sorting module that integrates with the iMFC system. The module allows the system to increase the operation envelope by either concentrating a dilute cell concentration in a large volume (e.g., bacteria present in environmental samples at a few cells per ml) or sorting out select cells from a background of many cells (e.g., activated T cells from a population of peripheral blood mononuclear cells. Embodiments of the microsorter are further described below.

Sorter Design.

Sorters perform three key functions: alignment, detection, and sorting. Our designs (e.g. FIG. 9) incorporate multiple innovations, including the combination of hydrodynamic and inertial focusing for alignment, and the use of EAP actuation for rapid sorting. In conventional cell sorters, particles or cells are focused both horizontally and vertically using a coaxial sheath flow that pinches the sample stream in a tight line. Since most microfluidic devices are planar, they can only focus particles in one direction (i.e., horizontal); multilayer devices can focus particles vertically or laterally as well but are significantly more complex to manufacture. Without vertical focusing, particles can be distributed across the height of the channel, leading to variations in velocity and overlap. In our designs, we align horizontally in the cross region via hydrodynamic focusing and vertically in the long "neck" via inertial focusing. Inertial focusing occurs when the fluid velocity is sufficiently high to generate lift forces on particles [6]. The combination allows us to effectively align particles in a single-layer device, which retains our simple manufacturing approach.

For sorting, we first detect particles using fluorescence, where upon detection of a targeted particle, a voltage pulse is applied to one or more EAP actuators. The actuators create a transient cross flow that deflects targeted particles onto a new pathline that leads to the sort outlet, as shown in FIG. 9.

Figure 9:
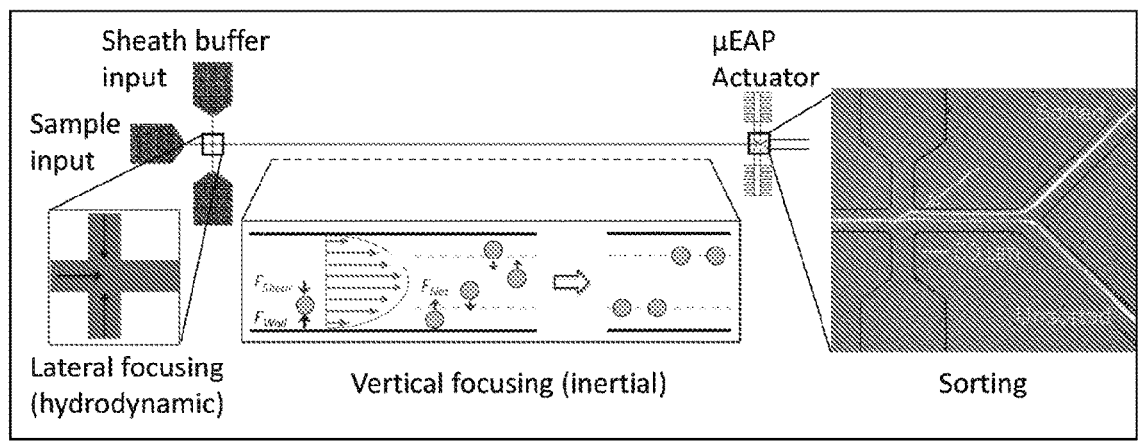
FIG. 9: EAP microsorter schematic showing the channel layout of the µEAP FACS.

FIG. 9. depicts (a) EAP microsorter schematic showing the channel layout of the μEAP FACS. The inset images illustrate the main functions of the channel. Horizontal alignment is accomplished by hydrodynamic focusing (left), while vertical alignment is achieved via inertial focusing (middle). Finally, targeted particles are sorted via the μEAP actuators (right). The extended exposure image shows streaks from an unsorted and sorted particle. The flow rate was 8 μl/min (107 mm/s), and the actuation pulse was 1 ms at 400 V.

The use of paired actuators that operate 180° out of phase significantly improves performance by doubling the force applied to the fluid and reducing fluidic resistance, which is proportional to channel length. With two actuators, one "pulls" while the other "pushes" the fluid, and the fluid is displaced only along the short distance between the actuators (typically ~2 mm). In contrast, with a single actuator, the fluid displacement occurs from the actuator to the device outlets (~30 mm).

To test our μFACS devices, we use a detection and control system, which consists of an epifluorescent microscope, charge-coupled device (CCD) camera, photomultiplier tubes, field-programmable gate array (FPGA)-based data acquisition system, and voltage amplifiers.

Initial Particle Separation Demonstration.

Figure 10:
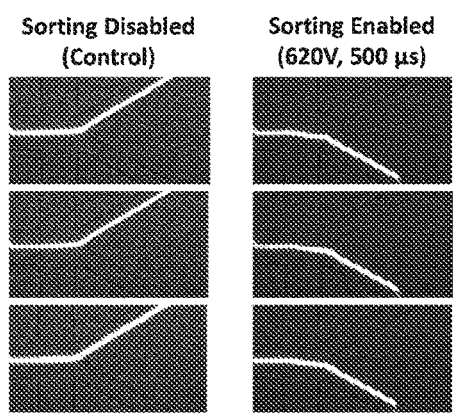
FIG. 10: Streak images of 7-µm green fluorescent particles.

To demonstrate the separation capabilities of the μEAP sorter, we sorted a mixture of green (7 μm) and red (5 μm) fluorescent particles by gating on the green fluorescence signal and applying a 620-V, 500-μs pulse to the EAP actuators. The fluid flow rate was 10 μl/min, which resulted in a mean linear velocity of 133 mm/s. Unsorted cells followed their default path to the waste channel, while sorted cells were deflected to a pathline that exited through the sort channel (FIG. 10). We captured 10-μl fluid volumes from both channel outlets with sorting disabled and enabled. The volumes were imaged in separate manual cytometers. Based on the cytometer results, we estimated a purity of 100% and yield of 93%.

Actuator Performance Optimization.

Following our initial proof of concept, we initiated a design study of the EAP fluidic actuators to improve our sorting throughput. We developed simplified electromechanical models of the actuators using COMSOL Multiphysics. Our results indicated that most actuation occurs at the perimeter of the devices. Based on these results, we developed a range of actuator designs and empirically tested their performance. By increasing the applied voltage and modifying the actuator geometry, we were able to improve the performance of the EAP actuators. We successfully sorted particles at a flow rate of 30 μl/min (400 mm/s) with a 25-μs, 800 V pulse, a 20-fold improvement over the sorter used in our initial particle separation demonstration.

Cell-Sorting Demonstration.

Figure 11:
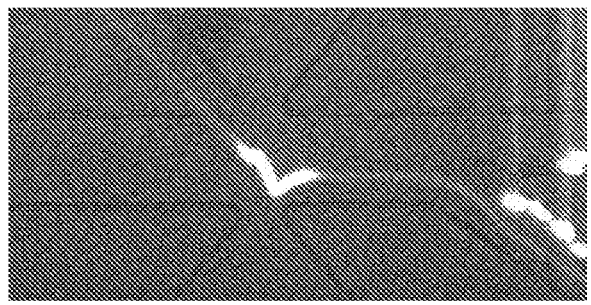
FIG. 11: Sorting of a phycoerythrin-labeled B-cell.
Figure 12:
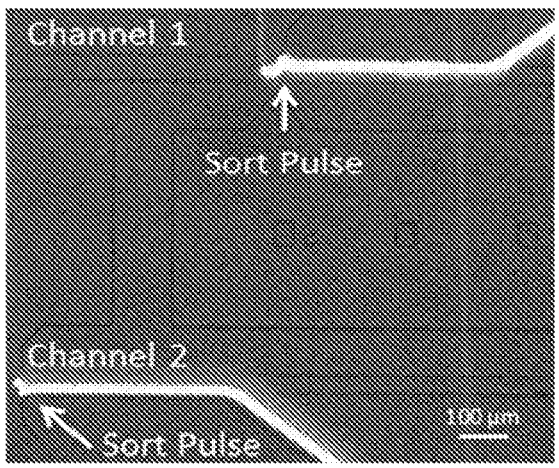
FIG. 12: Integration of multiple sorters into the dual-channel device.

To demonstrate cell separation within the μEAP FACS, we prepared a sample of mouse lymphocytes with fluorescently labeled B cells. The white blood cells were separated via centrifugation and then fixed prior to labeling with phycoerythrin-conjugated B220 antibody. The sample was input into the FACS. FIG. 11 shows an image of a sorted B cell. Sorting was performed with a 100-μs, 800-V pulse, at 11 μl/min (147 mm/s). Note that the fluorescent streak is brightest in the center. Since the labeled cells are significantly dimmer than fluorescent particles, we used a 488-nm diode laser to illuminate the cell in the detection region, while the dimmer light-emitting diode (LED) lamp provided full-field-of-view illumination. The bright spots to the right are cells that were trapped on the wall by a contaminating filament.

Multi-Sorter Integration.

Due to its straightforward fabrication and compatibility with soft lithography, the μEAP sorter can be easily integrated into more complex devices. To illustrate the integration capabilities of our EAP actuators, we developed additional devices featuring multiple independent sorters. FIG.

Figure 13:
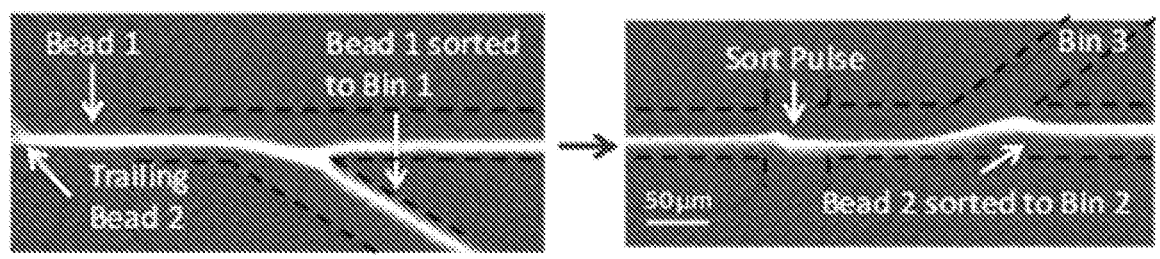
FIG. 13: Integration of multiple sorters into a staged sorting device.

12 shows parallel sorting in a dual-channel device, wherein extended time exposure shows two particles independently sorted in parallel channels, and FIG. 13 shows dual-stage serial sorting into multiple outlets, wherein extended time exposure shows two particles sorted by two serial sorters into one of three bins—note: Bin 3 was the default (unsorted) bin. Higher order multiple channel parallel and multistage serial sorting configurations are analogously constructed.

Our microfluidic fluorescence-activated cell sorter (µFACS) provides all the functions needed to sort particles: aligns the particles, detects their fluorescent signals, makes sort decisions based on fluorescence, and then sorts appropriately. Demonstrated capabilities include: particle sorting with multiple actuator pulse lengths as low as 20 µs; sorting with both multiple- and single-actuator configurations; independent parallel sorting in a multiple channel sorter; sequential sorting in a multi-stage sorters. Benefits of micro electroactive polymer (µEAP) sorters include: (a) Sorting is rapidly triggered via a simple electrical input (20 µsec sorting demonstrated); (b) µEAP actuators are compatible with a variety of microfabrication techniques; and (c) µEAP sorters are easily integrated, parallelizable, and well-suited for portable-scale devices

REFERENCES

[1] H. M. Shapiro, Practical Flow Cytometry, John Wiley & Sons, 2003.
[2] M. E. Piyasena and S. W. Graves, "The intersection of flow cytometry with microfluidics and microfabrication," Lab on a Chip, 14, 1044-1059, 2014.
[3] Y. Chen, T.-H. Wu, Y.-C. Kung, M. A. Teitell, and P.-Y. Chiou, "3D pulsed laser-triggered high-speed microfluidic fluorescence-activated cell sorter," Analyst, 138, 7308-7315, 2013.
[4] A. K. Price, K. M. Anderson, and C. T. Culberson, "Demonstration of an integrated electroactive polymer actuator on a microfluidic electrophoresis device," Lab on a Chip, 9, 2076-2084, 2009.
[5] C. Murray, D. McCoul, E. Sollier, T. Ruggiero, X. Niu, Q. Pei, D. Di Carlo, "Electro-adaptive microfluidics for active tuning of channel geometry using polymer actuators," Microfluidics and Nanofluidics, 14, 345-358, 2013.
[6] D. Di Carlo, D. Irimia, R. G. Tompkins, and M. Toner, "Continuous inertial focusing, ordering, and separation of particles in microchannels," Proceedings of the National Academy of Sciences, 104, 18892-18897, 2007.

Embodiments of our claimed invention include:

1. A high performance microfluidic electroactive polymer (µEAP) actuator configured about a flow channel wherein a voltage pulse applied to the actuator induces the actuator to create across the flow channel a transient cross flow that deflects targeted particles within the flow channel onto a new pathline, wherein the actuator comprises a dead-end fluid chamber in which a surface of the chamber comprises an electrode covered with an EAP layer of dielectric elastomer.

2. A plurality of actuators according to claim 1 configured about the flow channel and out of phase with each other, wherein a voltage pulse applied to the actuators induces the actuators to create across the flow channel a transient cross flow that deflects targeted particles within the flow channel onto a new pathline, wherein each actuator comprises a dead-end fluid chamber in which a surface of the chamber comprises an electrode covered with an EAP layer of dielectric elastomer.

3. A pair of actuators according to claim 1 configured about the flow channel and 180° out of phase with each other, wherein a voltage pulse applied to the actuators induces the actuators to create across the flow channel a transient cross flow that deflects targeted particles within the flow channel onto a new pathline, wherein each actuator comprises a dead-end fluid chamber in which a surface of the chamber comprises an electrode covered with an EAP layer of dielectric elastomer.

4. The actuator(s) of a foregoing or subsequent claim wherein a plurality of surfaces of the chamber(s) comprise an electrode covered with a EAP layer of dielectric elastomer.

5. The actuator(s) of a foregoing or subsequent claim wherein the flow channel is configured to provide a combination of hydrodynamic focusing for horizontal alignment and inertial focusing for vertical alignment of the particles.

6. The actuator(s) of a foregoing or subsequent claim wherein the new pathline leads to a sort outlet.

7. The actuator(s) of a foregoing or subsequent claim wherein the flow channel comprises a sample input channel and sorted and unsorted output channels and the new pathline leads to the sorted output channel.

8. The actuator(s) of a foregoing or subsequent claim wherein the flow channel is configured for fluorescence detection, whereupon detection of the targeted particles, the voltage pulse is applied to the µEAP actuators.

9. The actuator(s) of a foregoing or subsequent claim wherein the EAP layer is 1-50 (or 2-25, or 5-15 µm thick).

10. The actuator(s) of a foregoing or subsequent claim wherein the elastomer is silicone.

11. The actuator(s) of a foregoing or subsequent claim configured to provide parallel sorting in a multi-channel device.

12. The actuator(s) of a foregoing or subsequent claim configured to provide multi-stage serial sorting into multiple outlets.

13. The actuator(s) of a foregoing claim functionally integrated in a fluorescence-activated particle sorter.

14. A method using the actuator(s) of a foregoing claim comprising the step of applying a voltage pulse to induce the actuator(s) to create across the flow channel a transient cross flow that deflects targeted particles within the flow channel onto a new pathline.

The invention encompasses all combinations of recited particular and preferred embodiments. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:
1. An apparatus comprising:
a flow channel;
an electroactive polymer (EAP) actuator; and
a fluid chamber in fluidic communication with the flow channel and having a surface defined by the EAP actuator, the fluid chamber being a dead-end fluid chamber configured and arranged with a fluid path to communicate fluid to and from the flow channel, and wherein:
the EAP actuator includes an electrode and a dielectric layer; and the dielectric layer is responsive to a variable voltage applied to the electrode by a change in a dimension of the dielectric layer, the dielectric layer being configured to distort such that the EAP actuator is configured to draw fluid into the dead-end fluid chamber in response to the variable voltage being applied to the electrode and the EAP actuator is configured to push fluid from the dead-end fluid chamber in response to removal of the variable voltage.

2. The apparatus of claim 1, wherein the apparatus is a sorting apparatus, and the electrode of the EAP actuator is on the surface of the dead-end fluid chamber, the electrode being covered by the dielectric layer, wherein the variable voltage comprises a voltage pulse, and the dielectric layer is configured to transition between a compressed state and an expanded state in response to the voltage pulse, and in response to the change in the dimension of the dielectric layer, the EAP actuator is configured with the dead-end fluid chamber and the flow channel to sort particles contained in the fluid by creating a transient cross flow in the flow channel responsive to the change in the dimension of the dielectric layer.

3. The apparatus of claim 2, further including at least a first output channel and a second output channel in fluidic communication with the flow channel, wherein the electrode is configured to receive the voltage pulse in response to detection of a particle in the flow channel and the transition of the dielectric layer between the compressed state and the expanded state causes a change in movement of the particle through the flow channel, and wherein the EAP actuator is configured to sort the particles by aligning respective particles on a first pathline toward the first output channel when in the compressed state and aligning respective particles on a second pathline toward the second output channel when in the expanded state.

4. The apparatus of claim 2, wherein the apparatus is a sorting apparatus, and the compressed state and the expanded state comprise one or more changes in shape of the dielectric layer, wherein the EAP actuator is configured to deflect respective particles of the particles contained in the fluid onto a revised pathline in response to the transition between the compressed state and the expanded state.

5. The apparatus of claim 1, wherein fluid in the flow channel acts as another electrode.

6. The apparatus of claim 1, further comprising a voltage source configured to generate pulses having a pulse length in a range of about twenty microseconds to about one hundred microseconds, and in response to the pulses, the EAP actuator is configured with the dead-end fluid chamber and the flow channel to sort particles contained in the fluid by, responsive to the change in the dimension of the dielectric layer, generating lift forces on the particles to vertically align the particles in the flow channel as the particles are moving horizontally along the flow channel.

7. The apparatus of claim 1, wherein the flow channel, the dead-end fluid chamber, and the EAP actuator are configured and arranged together to:
align particles contained in the fluid flowing along the flow channel in two directions,
detect the particles within the flow channel using fluorescence, and
in response to detecting the particles, apply the variable voltage to the EAP actuator to sort the particles.

8. The apparatus of claim 7, wherein the flow channel, the dead-end fluid chamber, and the EAP actuator are further configured and arranged together to align particles in one direction using a hydrodynamic focusing technique and align the particles in another direction using an inertial focusing technique.

9. The apparatus of claim 7, further comprising a sample input port and two buffer input ports that respectively intersect at the flow channel, wherein the sample input port and two buffer input ports are configured and arranged with the flow channel to align particles contained in the fluid flowing within the flow channel in at least one of the two directions.

10. The apparatus of claim 1, further comprising another EAP actuator and another dead-end fluid chamber, and wherein each of the dead-end fluid chambers is in fluidic communication with the flow channel, and wherein the variable voltages applied to the EAP actuators are configured and arranged to be out of phase with respect to one another.

11. The apparatus of claim 10, wherein the dead-end fluid chambers are configured and arranged to generate a cross flow within the flow channel and deflect particles onto a revised pathline to sort the particles.

12. The apparatus of claim 1, wherein the flow channel, the dead-end fluid chamber, and the EAP actuator are configured and arranged together to align particles in the fluid in a direction along the flow channel via inertial focusing by generating lift forces on the particles.

13. The apparatus of claim 1, wherein the flow channel includes a plurality of channels and EAP actuators such that each flow channel, the dead-end fluid chamber, and the EAP actuator are configured and arranged together to provide parallel particle sorting across the plurality of channels.

14. The apparatus of claim 1, wherein the flow channel further includes a plurality of sorted output channels and EAP actuators in a plurality of dead-end chambers, and the flow channel, the dead-end fluid chambers, and the EAP actuators are configured and arranged together to provide a multi-stage serial sorting to the plurality of sorted output channels.

15. The apparatus of claim 1, wherein the flow channel, the dead-end fluid chamber, and the EAP actuator are configured and arranged together to detect target particles within the flow channel via fluorescence detection.

16. The apparatus of claim 1, wherein the flow channel, the dead-end fluid chamber, and the EAP actuator are configured and arranged together to sort particles within the fluid at a flow rate of 30 µl/min (400 mm/s) with a 25-µs voltage pulse.

17. The apparatus of claim 1, where the EAP actuator includes a dielectric or electroactive polymer layer with a thickness of at least one of: 1-50, 2-25, or 5-15 µm.

18. An apparatus comprising:
a flow channel;
an electroactive polymer (EAP) actuator; and
a fluid chamber in fluidic communication with the flow channel and having a surface defined by the EAP actuator, wherein:
the EAP actuator includes an electrode on the surface of the fluid chamber, the electrode being covered by a dielectric layer; and
the dielectric layer is responsive to a variable voltage applied to the electrode by a change in a dimension of the dielectric layer; and
a plurality of output channels in fluidic communication with the flow channel and the fluid chamber, wherein the EAP actuator is further configured and arranged to deflect a particle in the flow channel onto one of the plurality of output channels.

19. The apparatus of claim 18, wherein the apparatus is a sorting apparatus, and the change in the dimension of the dielectric layer causes a change in movement of fluid within the flow channel includes drawing fluid into the fluid chamber and out of the fluid chamber in response to the variable voltage and the fluid chamber is a dead-end fluid chamber.

20. An apparatus comprising:
a flow channel;
an electroactive polymer (EAP) actuator; and
a fluid chamber in fluidic communication with the flow channel and having a surface defined by the EAP actuator, wherein:
the EAP actuator includes an electrode on the surface of the fluid chamber and a dielectric layer; and
the dielectric layer is responsive to a variable voltage applied to the electrode by a change in a dimension of the dielectric layer and wherein the EAP actuator is configured and arranged with the flow channel to create a cross flow across the flow channel in response to the variable voltage, and wherein the cross flow results in deflection of particles within the flow channel onto a revised pathline.

21. The apparatus of claim 20, wherein the apparatus is a sorting apparatus, and the EAP actuator comprises a dielectric elastomer layered on the electrode and the fluid chamber is a dead-end fluid chamber.

* * * * *